(12) United States Patent
Yabe et al.

(10) Patent No.: US 11,638,791 B2
(45) Date of Patent: May 2, 2023

(54) SYRINGE TYPE EJECTION DEVICE

(71) Applicant: NIPRO CORPORATION, Osaka (JP)

(72) Inventors: Yukihiro Yabe, Osaka (JP); Teruhisa Hirobe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 674 days.

(21) Appl. No.: 16/500,608

(22) PCT Filed: Mar. 29, 2018

(86) PCT No.: PCT/JP2018/013202
§ 371 (c)(1),
(2) Date: Oct. 3, 2019

(87) PCT Pub. No.: WO2018/186277
PCT Pub. Date: Oct. 11, 2018

(65) Prior Publication Data
US 2020/0030552 A1 Jan. 30, 2020

(30) Foreign Application Priority Data
Apr. 4, 2017 (JP) .............................. JP2017-074296

(51) Int. Cl.
*A61M 11/00* (2006.01)
*A61M 15/08* (2006.01)

(52) U.S. Cl.
CPC .......... *A61M 11/007* (2014.02); *A61M 15/08* (2013.01)

(58) Field of Classification Search
CPC .. A61M 11/007; A61M 15/08; A61M 11/006; A61M 15/085
See application file for complete search history.

(56) References Cited

U.S. PATENT DOCUMENTS 3,491,757 A * 1/1970 Arce ...................... A61M 5/34
604/242
4,487,605 A * 12/1984 McGaughey ..... A61M 25/0693
604/168.01

(Continued)

FOREIGN PATENT DOCUMENTS

CA 2433769 A1 * 1/2004 ............ A61J 1/2096
CN 2079511 U 6/1991

(Continued)

OTHER PUBLICATIONS

Communication dated Apr. 23, 2021, from the China National Intellectual Property Administration in application No. 201880023736.7.

(Continued)

*Primary Examiner* — Nathan R Price
*Assistant Examiner* — Mark A Igel
(74) *Attorney, Agent, or Firm* — Sughrue Mion, PLLC

(57) ABSTRACT

A syringe type ejection device capable of reducing an amount of residual liquid is provided. A syringe type ejection device includes: a barrel; a nozzle disposed to face the barrel; and a core inserted in the nozzle, the barrel having a large-diameter portion provided with a discharge space for discharging liquid, the nozzle being provided with a holding space for holding the core, the holding space being in communication with the discharge space, and the core being inserted in the discharge space.

8 Claims, 33 Drawing Sheets

(56) References Cited

U.S. PATENT DOCUMENTS

| | | | | |
|---|---|---|---|---|
| 4,619,613 | A * | 10/1986 | Dragan | B05C 17/00579 433/90 |
| 4,941,876 | A * | 7/1990 | Meyer | A61M 5/2448 604/416 |
| 5,071,413 | A * | 12/1991 | Utterberg | A61M 5/162 604/905 |
| 5,154,325 | A | 10/1992 | Ryder et al. | |
| 5,238,153 | A | 8/1993 | Castillo et al. | |
| 5,601,077 | A * | 2/1997 | Imbert | B05B 11/007 128/200.22 |
| 5,961,489 | A | 10/1999 | Hirota | |
| 6,234,365 | B1 | 5/2001 | Bougamont et al. | |
| 6,427,878 | B1 * | 8/2002 | Greiner-Perth | B05B 11/02 604/209 |
| 6,475,206 | B1 * | 11/2002 | Hama | A61J 1/2089 604/413 |
| 6,789,750 | B1 * | 9/2004 | Heldt | B05B 1/3457 239/602 |
| 6,901,975 | B2 * | 6/2005 | Aramata | A61J 1/2096 141/319 |
| 10,661,033 | B2 * | 5/2020 | Yeates | B05B 7/068 |
| 2002/0174864 | A1 * | 11/2002 | Alchas | A61M 11/007 128/200.14 |
| 2002/0174865 | A1 * | 11/2002 | Gatton, Jr. | A61M 15/08 128/200.18 |
| 2003/0023207 | A1 | 1/2003 | Donnan et al. | |
| 2003/0111552 | A1 * | 6/2003 | Vedrine | A61M 5/284 239/533.1 |
| 2005/0199654 | A1 | 9/2005 | Andersen | |
| 2006/0085027 | A1 * | 4/2006 | Santin | A61F 5/56 606/199 |
| 2006/0124778 | A1 * | 6/2006 | Vendrine | A61M 5/2429 239/602 |
| 2009/0065527 | A1 | 3/2009 | Buck | |
| 2011/0046561 | A1 | 2/2011 | Pickhard | |
| 2012/0126035 | A1 * | 5/2012 | Greiner-Perth | A61M 11/007 222/321.6 |
| 2013/0096493 | A1 * | 4/2013 | Kubo | A61M 3/0262 604/212 |
| 2013/0298902 | A1 * | 11/2013 | Denton | A61M 11/06 128/200.14 |
| 2014/0303565 | A1 * | 10/2014 | Kubo | A61M 3/00 604/208 |
| 2015/0032082 | A1 * | 1/2015 | Kudoh | A61M 5/30 604/500 |
| 2015/0329271 | A1 * | 11/2015 | Toma | A61M 3/0279 222/386 |
| 2016/0068326 | A1 * | 3/2016 | Le Maner | A61M 15/0065 222/23 |
| 2017/0128364 | A1 * | 5/2017 | Kamishita | B05B 1/34 |

FOREIGN PATENT DOCUMENTS

| | | | | |
|---|---|---|---|---|
| CN | 1186699 | A | 7/1998 | |
| CN | 2382424 | Y | 6/2000 | |
| CN | 2822665 | Y | 10/2006 | |
| CN | 203525087 | U | 4/2014 | |
| CN | 203694276 | U | 7/2014 | |
| EP | 1084765 | A2 | 3/2001 | |
| EP | 1378223 | A1 * | 1/2004 | ............ A61J 1/2096 |
| EP | 1378223 | A1 | 1/2004 | |
| FR | 2 625 981 | A1 | 7/1989 | |
| FR | 2 793 708 | A1 | 11/2000 | |
| JP | 02-91553 | U | 7/1990 | |
| JP | 04-312462 | A | 11/1992 | |
| JP | 11-114065 | A | 4/1999 | |
| JP | 2001-135283 | A | 5/2001 | |
| JP | 2001-137344 | A | 5/2001 | |
| JP | 2001-523533 | A | 11/2001 | |
| JP | 2004-052817 | A | 2/2004 | |
| JP | 2005143677 | A * | 6/2005 | ............ A61J 1/2096 |
| JP | 3156168 | U | 12/2009 | |
| JP | 2014-046040 | A | 3/2014 | |
| JP | 2014-140588 | A | 8/2014 | |
| JP | 2014-140616 | A | 8/2014 | |
| JP | 2015-123297 | A | 7/2015 | |
| JP | 2016-007409 | A | 1/2016 | |
| JP | 2016-516500 | A | 6/2016 | |
| JP | 2018149170 | A | 9/2018 | |
| WO | 90/02575 | A1 | 3/1990 | |
| WO | WO-9115303 | A2 * | 4/1991 | |
| WO | 9115303 | A2 | 10/1991 | |
| WO | WO-9115303 | A2 * | 10/1991 | |
| WO | 9211049 | A1 | 7/1992 | |
| WO | 2012/002398 | A1 | 1/2012 | |
| WO | WO-2012002398 | A1 * | 1/2012 | .......... A61M 11/007 |
| WO | WO-2012157582 | A1 * | 11/2012 | .......... A61M 11/007 |
| WO | 2013/125555 | A1 | 8/2013 | |

OTHER PUBLICATIONS

Partial Supplementary European Search Report dated Dec. 3, 2020 from the European Patent Office in Application No. 18781738.2.

Notice of Grounds of Rejection for Corresponding JP 2017-074296, dated Dec. 18, 2018.

Notice of Grounds of Rejection for Corresponding JP 2017-048673, dated Jan. 22, 2019.

Notice of Grounds of Rejection for Corresponding JP 2017-074296, dated Mar. 12, 2019.

Notice of Grounds of Rejection for Corresponding JP 2017-048673, dated Aug. 27, 2019.

International Search Report for PCT/JP2018/013202, dated May 29, 2018.

The Extended European Search Report dated Feb. 23, 2021, issued by the European Patent Office in application No. 18781738.2.

Communication dated May 23, 2022 from the China National Intellectual Property Administration in CN Partial Application No. 201880023736.7.

* cited by examiner

FIG.24
(a)
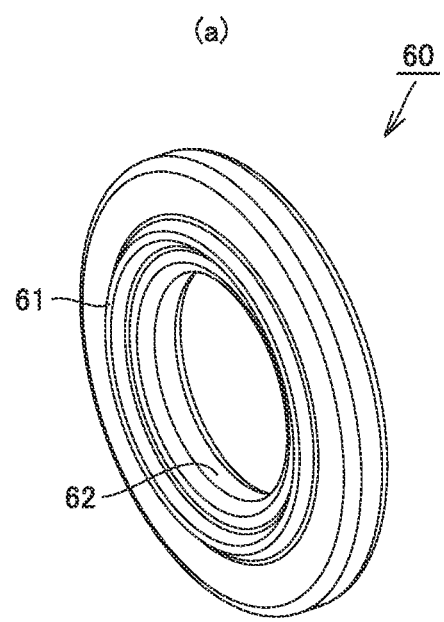
(b)
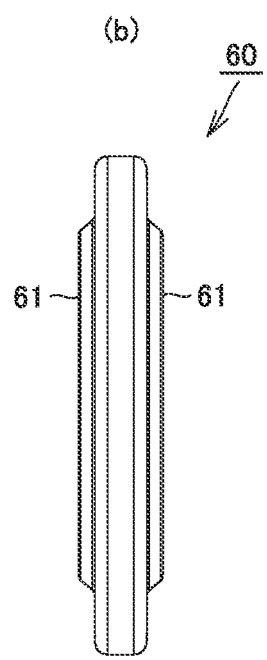

FIG.33
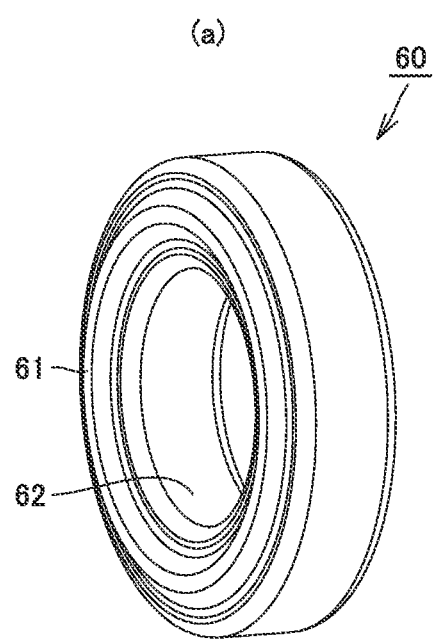
(a)
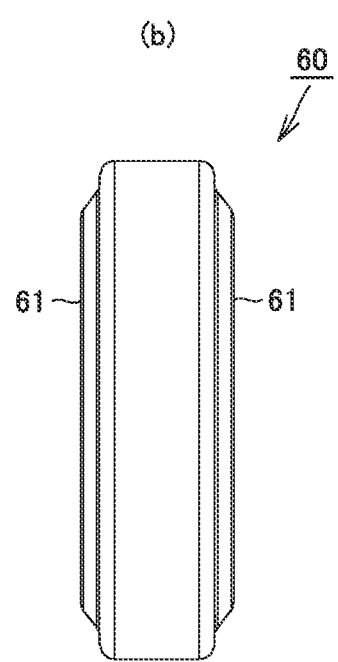
(b)

SYRINGE TYPE EJECTION DEVICE

This application is a National Stage of International Application No. PCT/JP2018/013202 filed Mar. 29, 2018, claiming priority based on Japanese Patent Application No. 2017-074296 filed Apr. 4, 2017.

TECHNICAL FIELD

The present invention relates to a syringe type ejection device.

BACKGROUND ART

Conventionally, a syringe type ejection device is described in Japanese Patent Laying-Open No. 2014-46040 (PTL 1) and Japanese Patent Laying-Open No. 2016-7409 (PTL 2), for example.

CITATION LIST

Patent Literature

PTL 1: Japanese Patent Laying-Open No. 2014-46040
PTL 2: Japanese Patent Laying-Open No. 2016-7409

SUMMARY OF INVENTION

Technical Problem

PTL 1 discloses a structure in which a cartridge fits over a tip end of an operation instrument.

PTL 2 discloses a syringe having a nozzle body portion fitting over its tip end.

One problem with a conventional syringe type ejection device was that liquid tends to leak from a fitting portion of a barrel and a nozzle.

Another problem with a conventional syringe type ejection device was that liquid tends to remain at a tip end portion of a gasket within the barrel.

The present invention has been made in view of the problems as described above. One object of the present invention is to provide a syringe type ejection device capable of preventing leakage of liquid. Another object of the present invention is to provide a syringe type ejection device capable of reducing an amount of residual liquid.

Solution to Problem

A syringe type ejection device according to one aspect of the present invention includes: a barrel; a nozzle disposed to face the barrel; and an annular packing interposed between the barrel and the nozzle, the barrel having a tip end portion provided with a discharge space for discharging liquid, the tip end portion including a first surface facing the nozzle, the nozzle being provided with a holding space for holding a core, the holding space being in communication with the discharge space, the nozzle including a second surface facing the first surface, the annular packing being provided to be in contact with the first surface and the second surface to enable movement of the liquid from the discharge space to the holding space, and the syringe type ejection device further including a biasing portion that biases the first surface and the second surface toward the annular packing.

In the syringe type ejection device thus structured, since the annular packing is provided to be in contact with the first surface and the second surface to enable movement of the liquid from the discharge space to the holding space, and the syringe type ejection device further includes the biasing portion that biases the first surface and the second surface toward the annular packing, the packing makes intimate contact with the first surface and the second surface. As a result, leakage of the liquid can be prevented.

Preferably, the biasing portion is provided on the nozzle. In this case, the biasing portion and the nozzle can be integrated together, leading to a reduced number of components.

Preferably, the biasing portion covers the tip end portion. In this case, since the biasing portion covers the tip end portion, leakage of the liquid from the tip end portion can be more effective prevented.

Preferably, the tip end portion has a large-diameter portion, and the biasing portion engages the large-diameter portion. In this case, the tip end portion has a flange shape, thus making it easier for the biasing portion to engage the flange shape.

Preferably, the biasing portion has a plurality of hooks that engage the large-diameter portion. In this case, the plurality of hooks engage the flange shape, thus allowing the flange shape to be biased by the plurality of hooks. As a result, the flange shape can be uniformly biased to effectively suppress leakage of the liquid.

Preferably, the biasing portion is flexible, and a through hole extending through a thickness of the nozzle is provided in a portion of the nozzle in proximity of the biasing portion. In this case, since the through hole is provided in a portion of the nozzle in proximity of the biasing portion, the biasing portion readily bends. As a result, the biasing portion can readily engage the flange shape.

Preferably, the first surface and the second surface are thrust surfaces. In this case, a seal can be formed at a shorter joint length than when the first surface and the second surface are radial surfaces (circumferential surfaces). As a result, the syringe type ejection device can be reduced in size.

Preferably, the core protrudes from the second surface and is inserted in the discharge space. In this case, the core can guide the barrel during assembly of the nozzle and the barrel, thus making the assembly easier.

A syringe type ejection device according to another aspect of the present invention includes: a barrel; a nozzle disposed to face the barrel; and a core inserted in the nozzle, the barrel having a tip end portion provided with a discharge space for discharging liquid, the nozzle being provided with a holding space for holding the core, the holding space being in communication with the discharge space, and the core being inserted in the discharge space.

In the syringe type ejection device thus structured, since the core is inserted in the discharge space, an amount of residual liquid in the discharge space can be reduced.

Preferably, the syringe type ejection device further includes an annular packing interposed between the barrel and the nozzle. In this case, leakage of the liquid from between the barrel and the nozzle can be prevented because of the provision of the packing.

Advantageous Effects of Invention

According to the present invention, a syringe type ejection device capable of preventing leakage of liquid can be provided.

According to the present invention, a syringe type ejection device capable of reducing an amount of residual liquid can be provided.

BRIEF DESCRIPTION OF DRAWINGS

FIG. 24 shows a perspective view (a) of a packing of the syringe type ejection device according to the third embodiment, and a side view (b) of the packing of the syringe type ejection device according to the third embodiment.

FIG. 33 shows a perspective view (a) of a packing of the syringe type ejection device according to the fourth embodiment, and a side view (b) of the packing of the syringe type ejection device according to the fourth embodiment.

DESCRIPTION OF EMBODIMENTS

Figure 1:
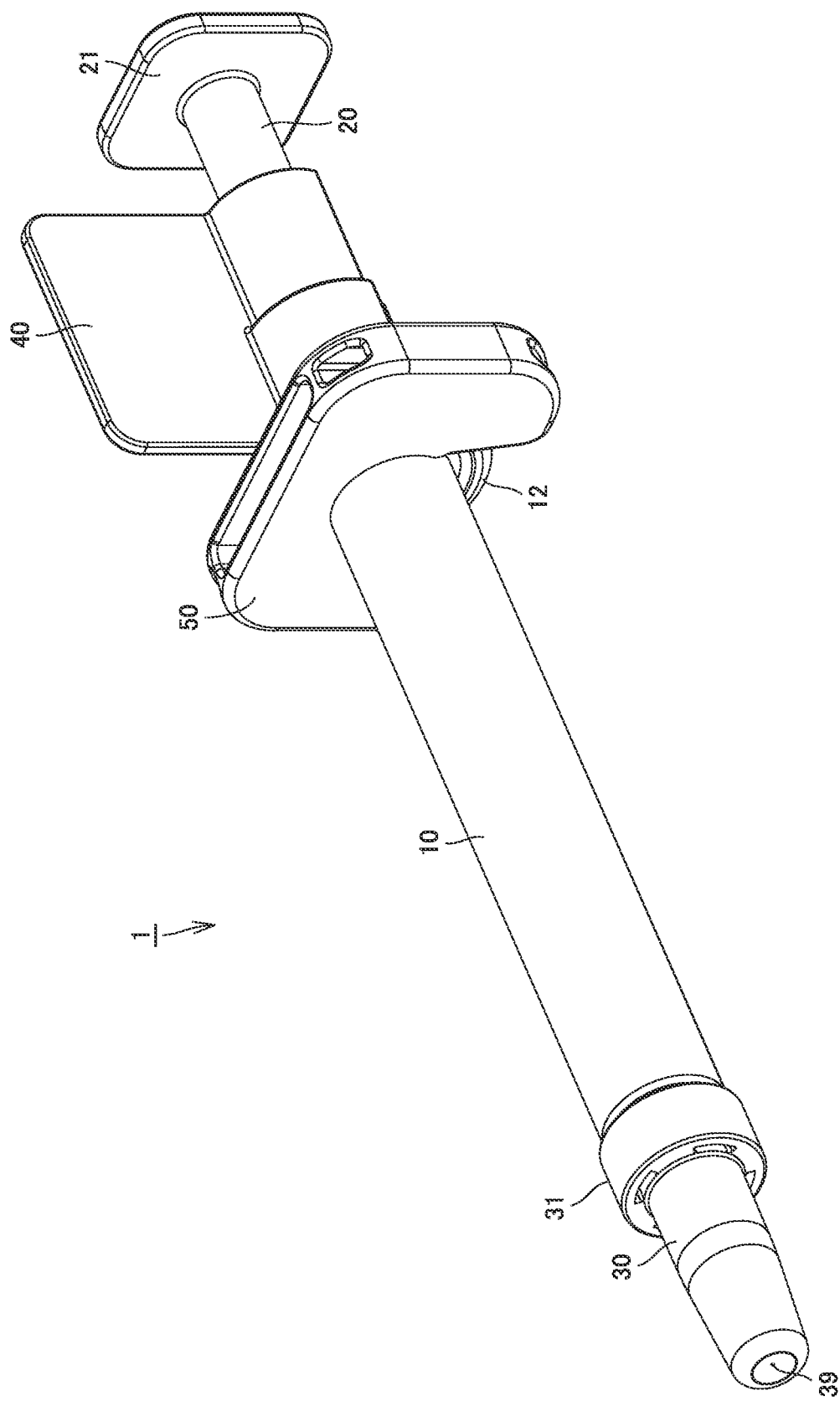
FIG. 1 is a perspective view of a syringe type ejection device according to a first embodiment.

Embodiments of the present invention are described below in detail with reference to the drawings. In the embodiments described below, the same or corresponding portions are denoted by the same characters in the drawings and description thereof will not be repeated.

First Embodiment (Structure)

Figure 2:
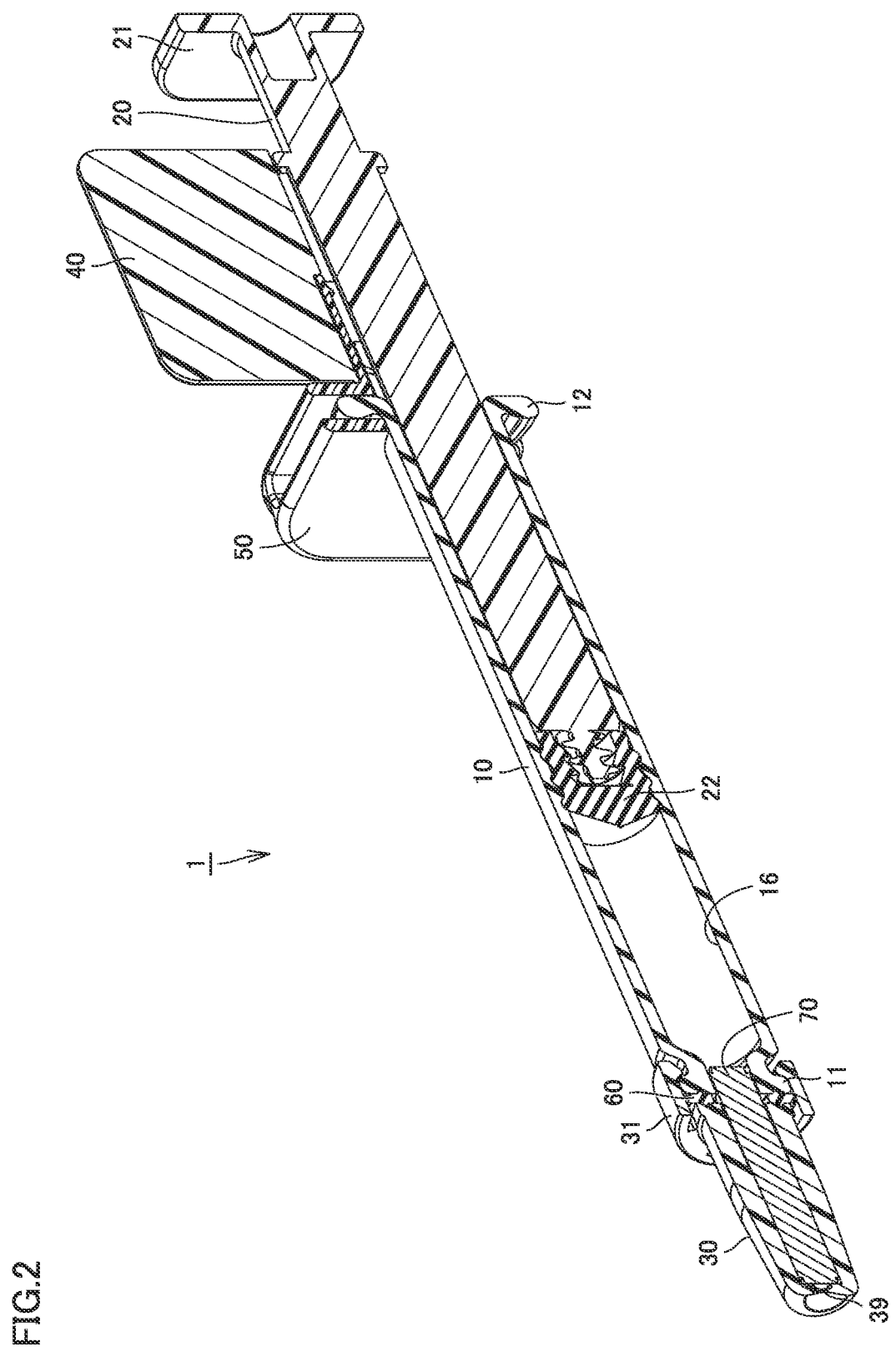
FIG. 2 is a perspective view including a partial cross section of the syringe type ejection device according to the first embodiment.

FIG. 1 is a perspective view of a syringe type ejection device according to a first embodiment. FIG. 2 is a perspective view including a partial cross section of the syringe type ejection device according to the first embodiment. As shown in FIGS. 1 and 2, a syringe type ejection device 1 includes a barrel 10, a packing 60 as a seal member, a nozzle 30, a core 70, a gasket 22, a stopper 40, a finger grip 50, and a plunger 20.

Barrel 10 extends from a large-diameter portion 11 as a tip end portion to flange 12. Barrel 10 is transparent or translucent. Barrel 10 is filled with liquid. Calibration marks indicating the amount of liquid may be provided on an outer circumferential surface of barrel 10.

Barrel 10 is made of glass, but may be made of plastic. The material for barrel 10 is determined depending on the liquid and a medicament stored in barrel 10.

Nozzle 30 is provided to face large-diameter portion 11. Nozzle 30 has a biasing portion 31. Biasing portion 31 covers large-diameter portion 11. Nozzle 30 is provided with an ejection hole 39 at its tip end. Core 70 is provided in its surface with a groove extending in a longitudinal direction of core 70. Thus, the liquid can move in the longitudinal direction of core 70 along the groove in the surface of core 70 even when core 70 is in contact with an inner circumferential surface of nozzle 30. The medicament in a bore 16 can be ejected from ejection hole 39 through the groove in core 70.

Packing 60 is disposed between nozzle 30 and large-diameter portion 11. Packing 60 has an annular shape. Packing 60 is made of an elastic body such as rubber or resin.

Finger grip 50 fits over flange 12. Finger grip 50 is intended to be held by a human hand. Finger grip 50 does not need to be provided when flange 12 is large enough to be held by a human.

Plunger 20 is inserted in bore 16 in barrel 10. Plunger 20 is in the form of a bar. Gasket 22 fits over a tip end of plunger 20. A rear end of plunger 20 forms a press portion 21.

Plunger 20 can move within barrel 10. The movement of plunger 20 within barrel 10 causes a change in volume of bore 16 from gasket 22 to large-diameter portion 11. The liquid is discharged from large-diameter portion 11 depending on this volume change.

Syringe type ejection device 1 is a capacity-defined syringe. Stopper 40 engages plunger 20. Stopper 40 serves to determine a dose of medicament by a single pumping. Stopper 40 is provided when the dose by a single pumping of plunger 20 needs to be limited. Stopper 40 does not need to be provided when the dose does not need to be limited.

When using syringe type ejection device 1 as a transnasal device, nozzle 30 is inserted in one of the nostrils and plunger 20 is pumped to eject the medicament from ejection hole 39. A stroke of the pumping is limited by stopper 40. Stopper 40 is removed from plunger 20, nozzle 30 is inserted in the other nostril and plunger 20 is pumped, to thereby eject the medicament into the other nostril from ejection hole 39.

Figure 3:
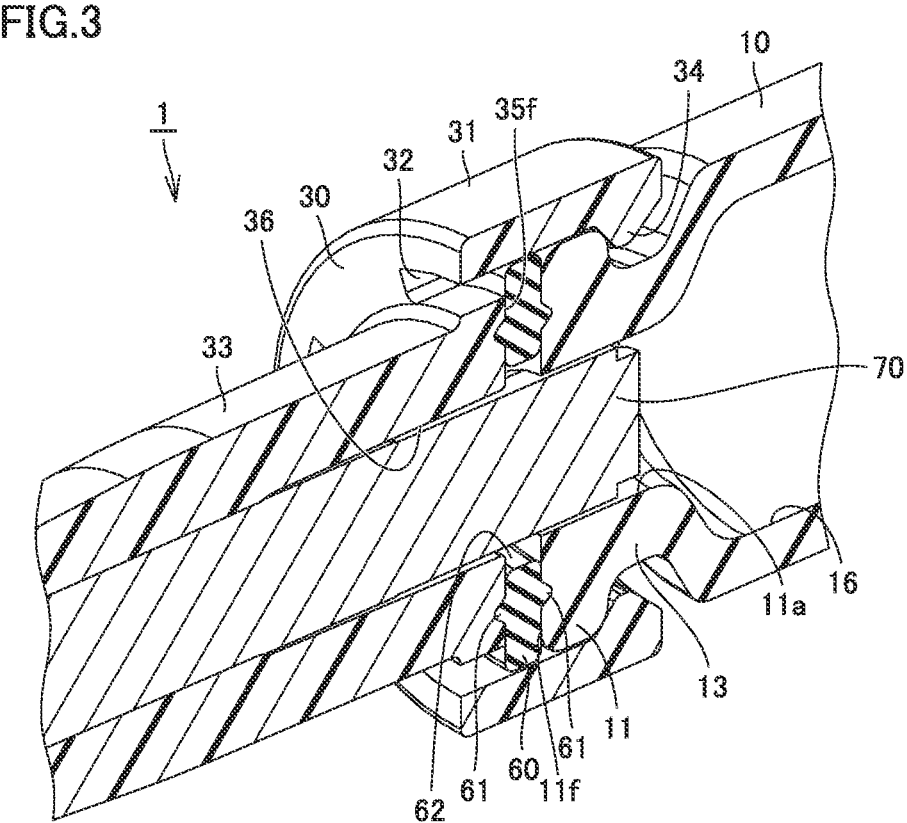
FIG. 3 is a perspective view including a partial cross section showing an enlarged engagement portion of a barrel and a nozzle of the syringe type ejection device according to the first embodiment.

FIG. 3 is a perspective view including a partial cross section showing an enlarged engagement portion of the barrel and the nozzle of the syringe type ejection device according to the first embodiment. As shown in FIG. 3, barrel 10 has a neck 13 having a small outer diameter. Large-diameter portion 11 is attached to neck 13. Neck 13 and large-diameter portion 11 are provided with a discharge space 11a.

A first surface 11f of large-diameter portion 11 is a surface that makes contact with packing 60 as an O ring.

A nozzle body 33 of nozzle 30 is provided with a holding space 36 which is a bore. Core 70 is stored in holding space 36. Core 70 is provided with a groove in its surface for delivering the medicament to the nozzle tip end. Core 70 protrudes from a rear end of nozzle 30. Thus, core 70 is inserted in large-diameter portion 11 and neck 13 at the tip end of barrel 10.

A rear end face of nozzle 30 is a second surface 35f. Second surface 35f faces first surface 11f.

Biasing portion 31 forms part of nozzle 30. Biasing portion 31 is provided with hooks 34 that engage large-diameter portion 11. Nozzle 30 is provided with through holes 32. Biasing portion 31 is thereby provided with flexibility.

Figure 4:
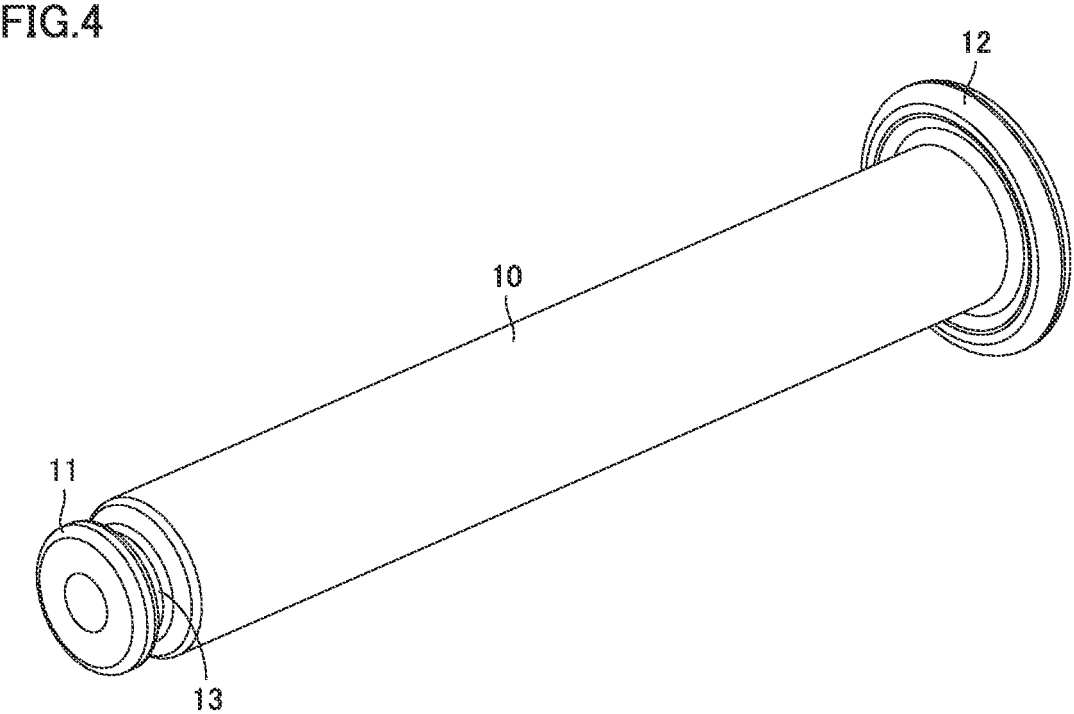
FIG. 4 is a perspective view of the barrel of the syringe type ejection device according to the first embodiment.

FIG. 4 is a perspective view of the barrel of the syringe type ejection device according to the first embodiment. Barrel 10 made of glass extends from large-diameter portion 11 to flange 12 in the longitudinal direction. Barrel 10 in a cylindrical shape has a constant inner diameter. Barrel 10 is not limited to have a cylindrical shape. The material for the barrel may be other than glass.

Figure 5:
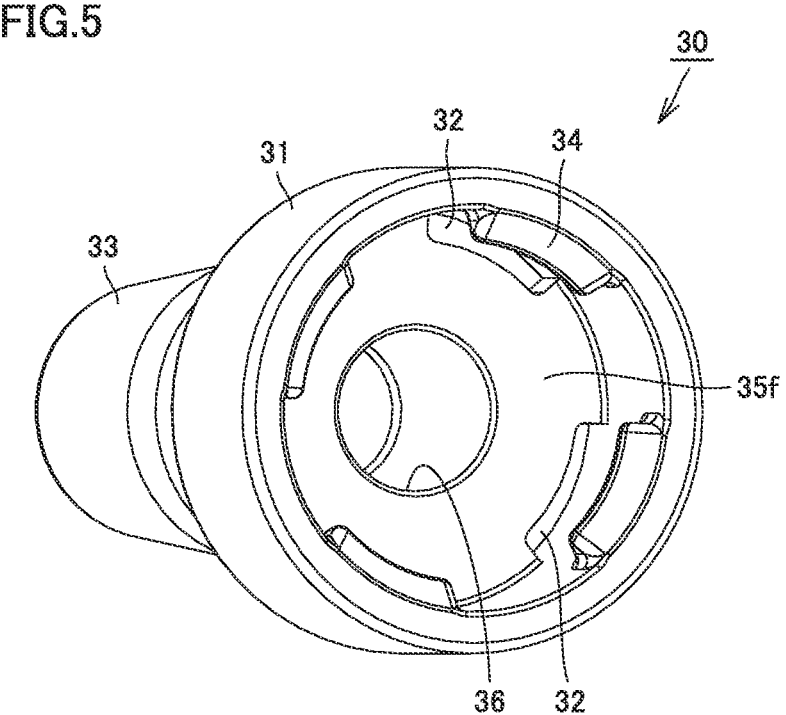
FIG. 5 is a perspective view of the nozzle of the syringe type ejection device according to the first embodiment.

FIG. 5 is a perspective view of the nozzle of the syringe type ejection device according to the first embodiment. As shown in FIG. 5, biasing portion 31 is at the rear end side of nozzle 30. Biasing portion 31 has an outer diameter greater than an outer diameter of nozzle body 33. The plurality of hooks 34 are provided at regular intervals in an inner space of biasing portion 31. Although biasing portion 31 is provided integrally with nozzle 30 in this embodiment, biasing portion 31 may be provided separately from nozzle 30.

The plurality of through holes 32 are provided in the outer circumference of second surface 35f. Each through hole 32 is provided at a position corresponding to each hook 34.

Figure 6:
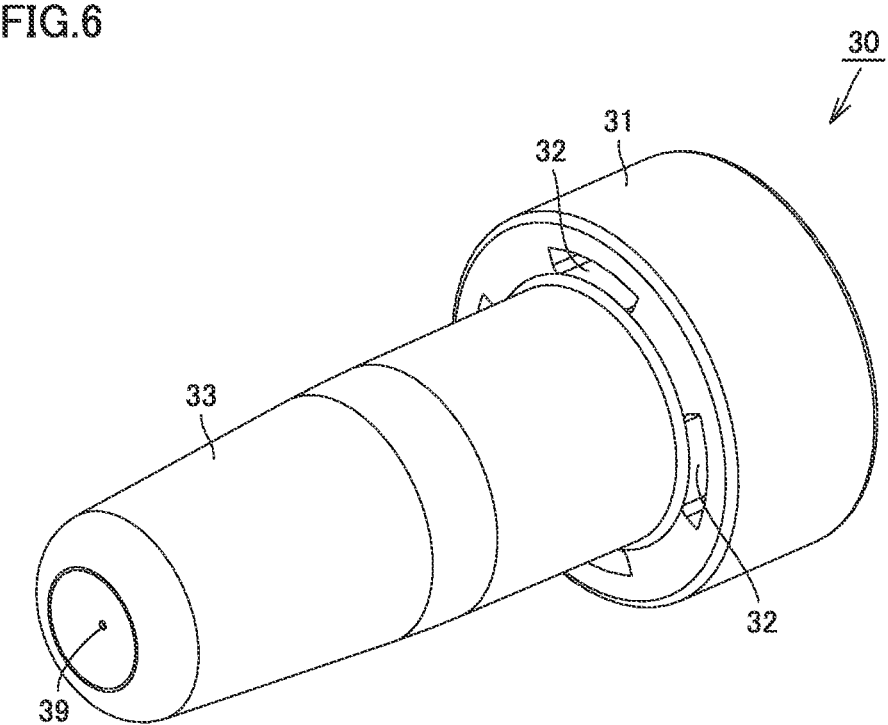
FIG. 6 is a perspective view of the nozzle of the syringe type ejection device according to the first embodiment.

FIG. 6 is a perspective view of the nozzle of the syringe type ejection device according to the first embodiment. As shown in FIG. 6, nozzle body 33 has an outer diameter that decreases toward its tip end, forming a so-called tapered shape. This is to allow the insertion of the tip end of nozzle body 33 in a nostril for ejection of the medicament into a nasal cavity.

Figure 7:
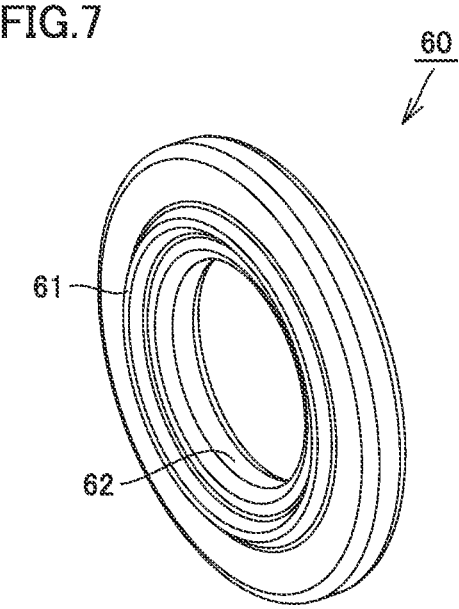
FIG. 7 is a perspective view of a packing of the syringe type ejection device according to the first embodiment.
Figure 8:
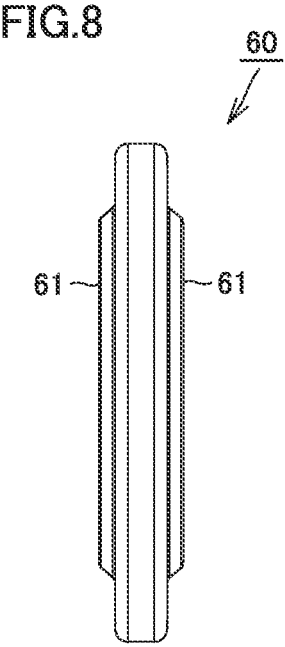
FIG. 8 is a side view of the packing of the syringe type ejection device according to the first embodiment.

FIG. 7 is a perspective view of the packing of the syringe type ejection device according to the first embodiment. FIG. 8 is a side view of the packing of the syringe type ejection device according to the first embodiment. As shown in FIGS. 7 and 8, packing 60 has a circular shape, with a through hole 62 provided at its center. Thrust surfaces of packing 60 facing each other are provided with a pair of annular convex portions 61. Because of the provision of convex portions 61, convex portions 61 are compressed by first surface 11f and second surface 35f to have a crushed shape. The effect of preventing leakage of the liquid is thereby increased.

Syringe type ejection device 1 includes barrel 10, nozzle 30 disposed at the tip end of barrel 10, and annular packing 60 interposed between barrel 10 and nozzle 30, barrel 10 has large-diameter portion 11 provided with discharge space 11a for discharging the liquid, large-diameter portion 11 includes the first surface facing nozzle 30, nozzle 30 is provided with holding space 36 for holding the core, holding space 36 is in communication with discharge space 11a, nozzle 30 includes second surface 35f facing first surface 11f, annular packing 60 is provided to be in contact with first surface 11f and second surface 35f to enable movement of the liquid from discharge space 11a to holding space 36, and syringe type ejection device 1 further includes biasing portion 31 that biases first surface 11f and second surface 35f toward annular packing 60.

Biasing portion 31 is provided on nozzle 30. Biasing portion 31 covers large-diameter portion 11. Biasing portion 31 engages large-diameter portion 11. Biasing portion 31 has the plurality of hooks 34 that engage large-diameter portion 11. Biasing portion 31 is flexible, and through holes 32 extending through the thickness of nozzle 30 are provided in portions of the nozzle in proximity of biasing portion 31. First surface 11f and second surface 35f are thrust surfaces. Core 70 protrudes from second surface 35f and is inserted in discharge space 11a.

When plunger 20 is pushed toward nozzle 30, the medicament in bore 16 is moved through the groove provided in the surface of core 70 and ejected from ejection hole 39. When using syringe type ejection device 1 as a transnasal device, nozzle 30 is inserted in a nostril and the medicament is sprayed into a nasal cavity.

(Effects)

In syringe type ejection device 1 thus structured, packing 60 is provided between first surface 11f and second surface 35f, and first surface 11f and second surface 35f are biased toward packing 60 by biasing portion 31. As a result, leakage of the liquid from between first surface 11f and second surface 35f can be prevented. As a result, a prescribed amount of medicament can be reliably sprayed.

Since first surface 11f and second surface 35f are thrust surfaces and packing 60 is disposed between them, the size in a radial direction of syringe type ejection device 1 can be made smaller than when packing 60 is provided on a radial surface. The inner diameter of discharge space 11a can be increased, thus making it easier to insert core 70 in the discharge space.

Since biasing portion 31 covers large-diameter portion 11, an area of contact between biasing portion 31 and large-diameter portion 11 is increased. As a result, large-diameter portion 11 can be reliably held by biasing portion 31.

Since the plurality of hooks 34 are flexible (elastic), and engage large-diameter portion 11 in the state shown in FIG. 3, the elasticity of biasing portion 31 can be utilized to press first surface 11f against packing 60.

Second Embodiment

Figure 9:
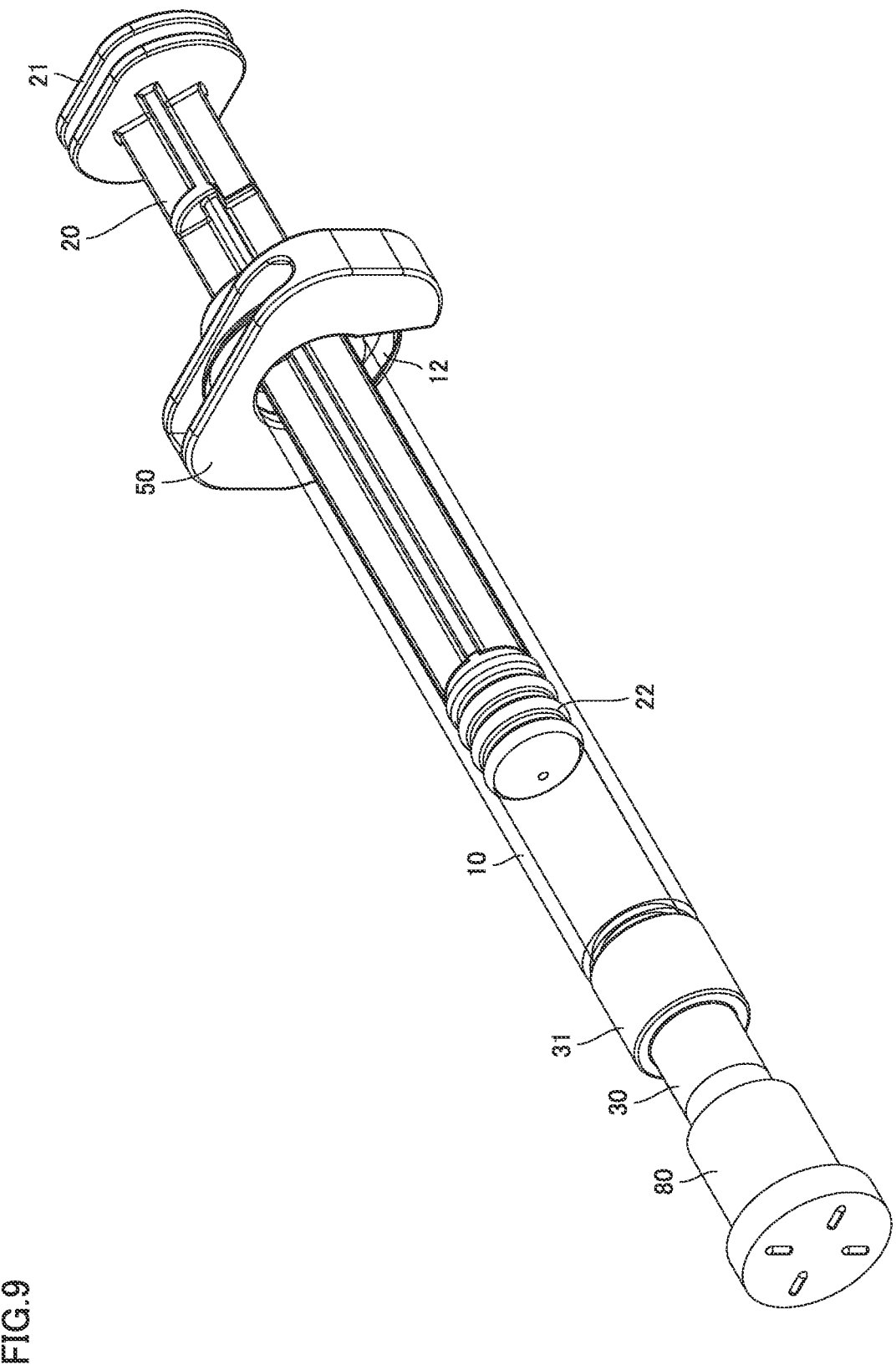
FIG. 9 is a perspective view of a syringe type ejection device according to a second embodiment.
Figure 10:
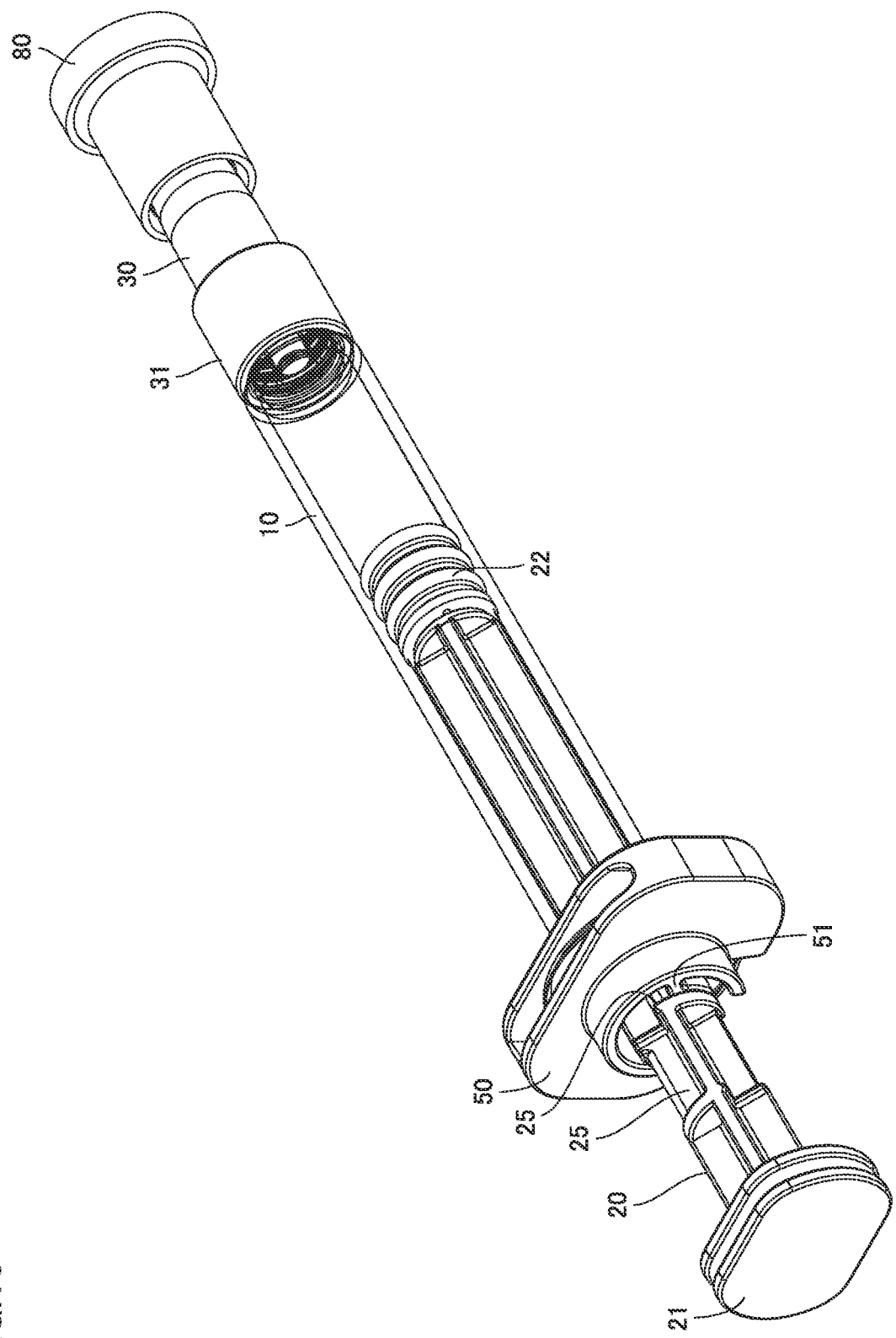
FIG. 10 is a perspective view of the syringe type ejection device according to the second embodiment.
Figure 11:
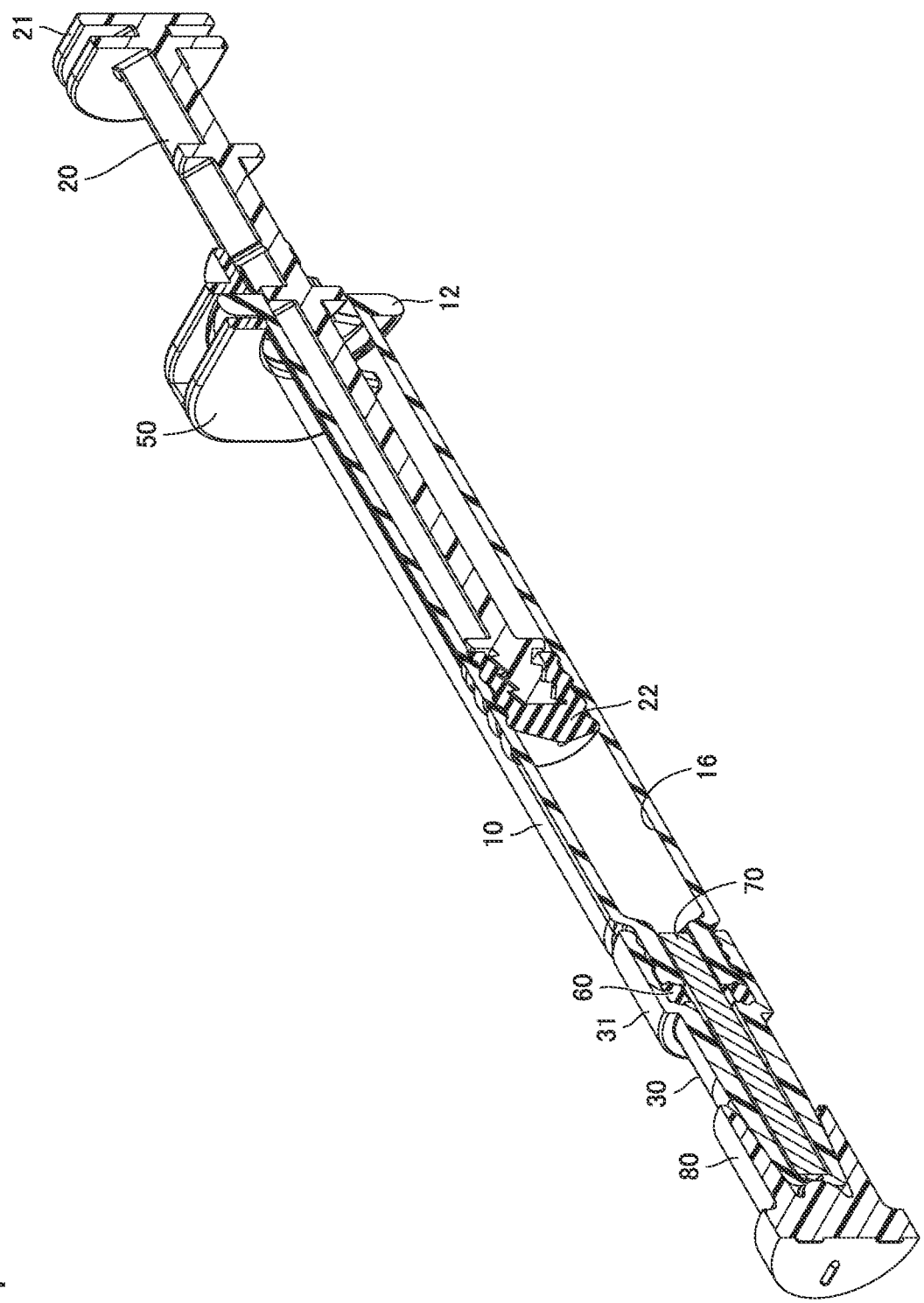
FIG. 11 is a perspective view including a partial cross section of the syringe type ejection device according to the second embodiment.

FIGS. 9 and 10 are perspective views of a syringe type ejection device according to a second embodiment. FIG. 11 is a perspective view including a partial cross section of the syringe type ejection device according to the second embodiment.

As shown in FIGS. 9 to 11, in syringe type ejection device 1 according to the first embodiment, plunger 20 is provided with a step 25. Step 25 engages a protrusion 51 of finger grip 50.

The engagement is released by rotation of plunger 20 from the state in which protrusion 51 and step 25 are in contact with each other as shown in FIG. 10. Plunger 20 can thereby be moved in an axial direction.

A nozzle cap 80 fits over the tip end of nozzle 30 in the second embodiment. Nozzle 30 may be covered with nozzle cap 80 in the first embodiment as well.

Figure 12:
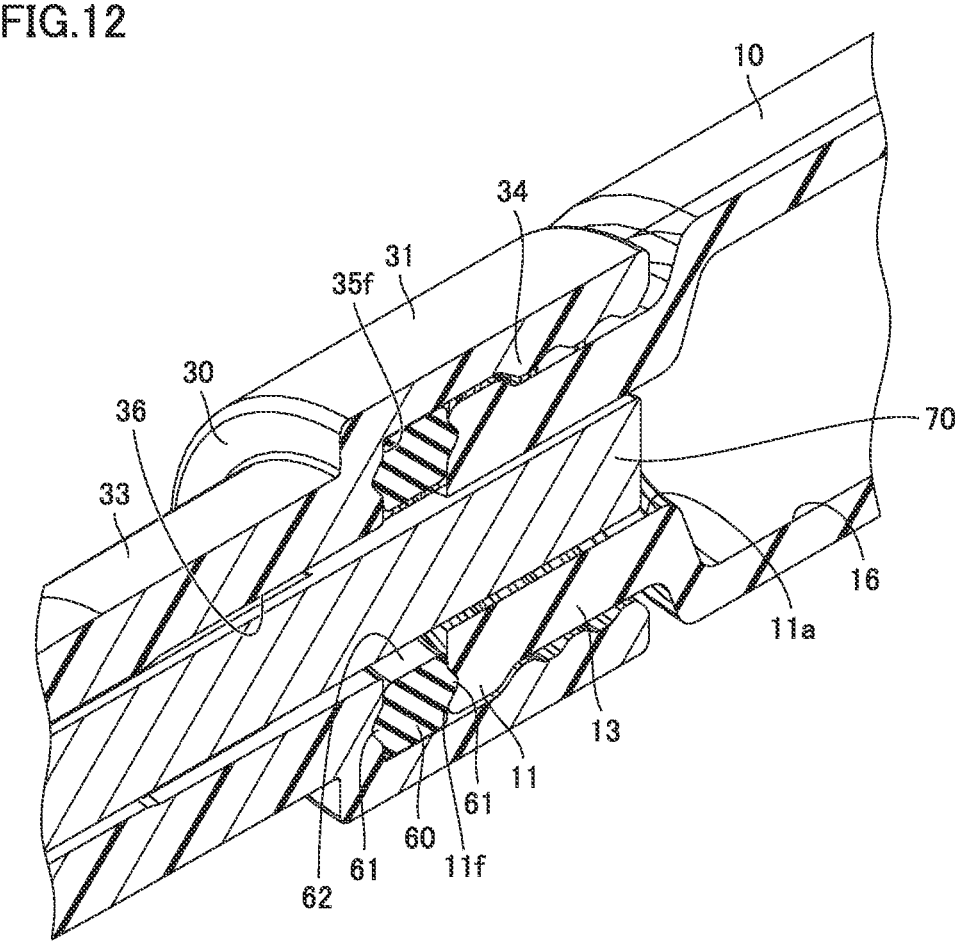
FIG. 12 is a perspective view including a partial cross section showing an enlarged engagement portion of a barrel and a nozzle of the syringe type ejection device according to the second embodiment.

FIG. 12 is a perspective view including a partial cross section showing an enlarged engagement portion of a barrel and the nozzle of the syringe type ejection device according to the second embodiment. As shown in FIG. 12, biasing portion 31 according to the second embodiment is longer than biasing portion 31 according to the first embodiment in the axial direction. Biasing portion 31 is provided with hooks 34 on its inner circumferential surface. Nozzle 30 is not provided with the through holes as were described in the first embodiment.

Figure 13:
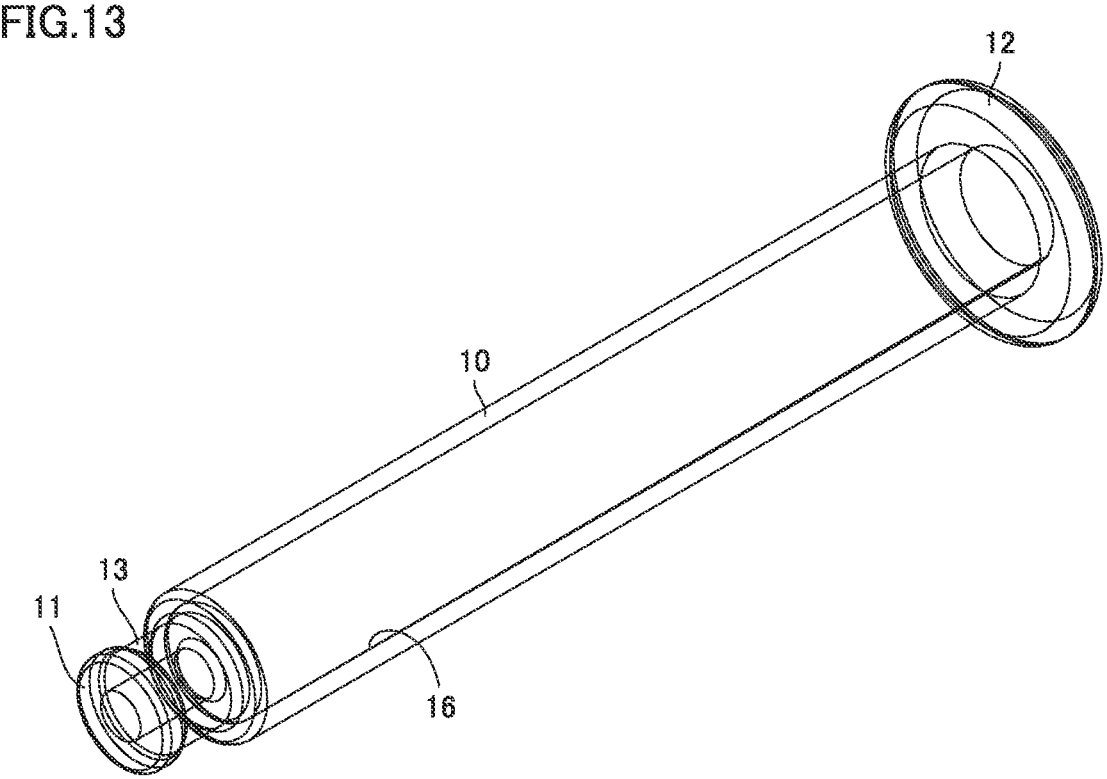
FIG. 13 is a perspective view of the barrel of the syringe type ejection device according to the second embodiment.

FIG. 13 is a perspective view of the barrel of the syringe type ejection device according to the second embodiment. As shown in FIG. 13, an internal structure of barrel 10 according to the second embodiment is shown in a perspective view.

When using liquid or a medicament that has to be kept away from light, barrel 10 is made of a light-shielding material.

Figure 14:
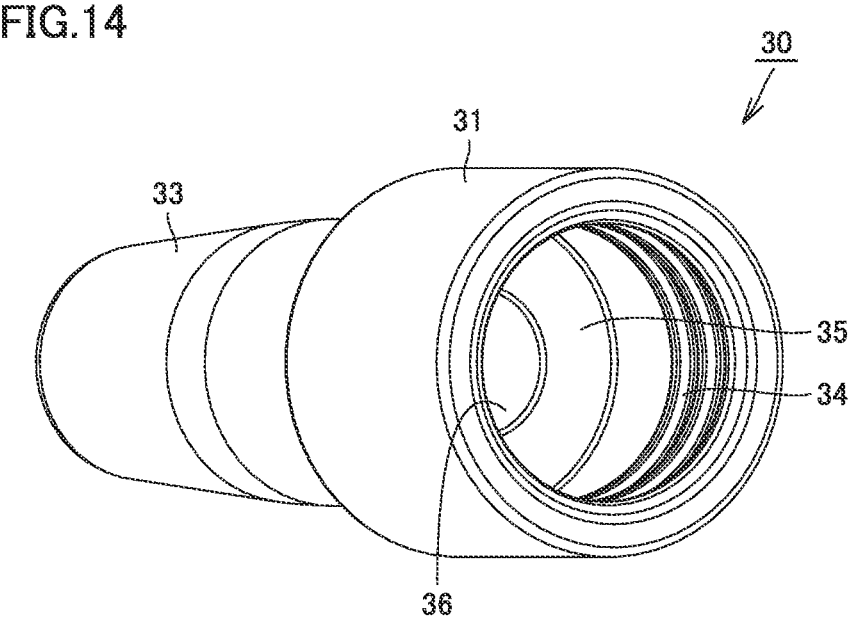
FIG. 14 is a perspective view of the nozzle of the syringe type ejection device according to the second embodiment.
Figure 15:
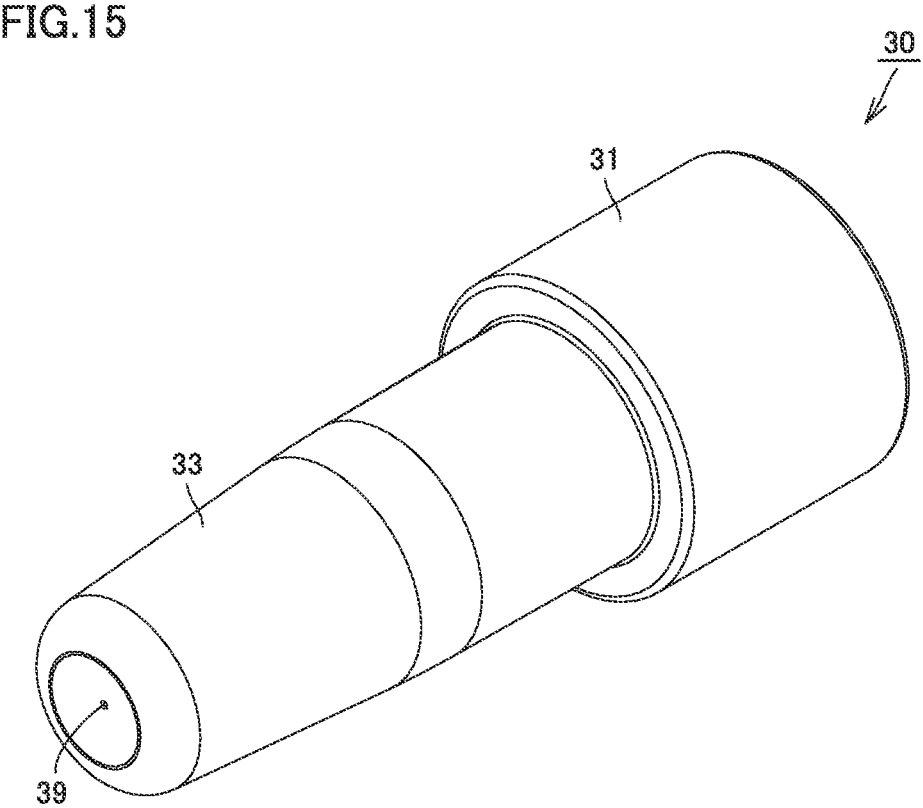
FIG. 15 is a perspective view of the nozzle of the syringe type ejection device according to the second embodiment.

FIGS. 14 and 15 are perspective views of the nozzle of the syringe type ejection device according to the second embodiment. As shown in FIGS. 14 and 15, nozzle 30 in the second embodiment has biasing portion 31 elongated in the axial direction. The difference from biasing portion 31 according to the first embodiment is that this biasing portion 31 is provided with annular hooks 34 on its inner circumferential surface.

Figure 16:
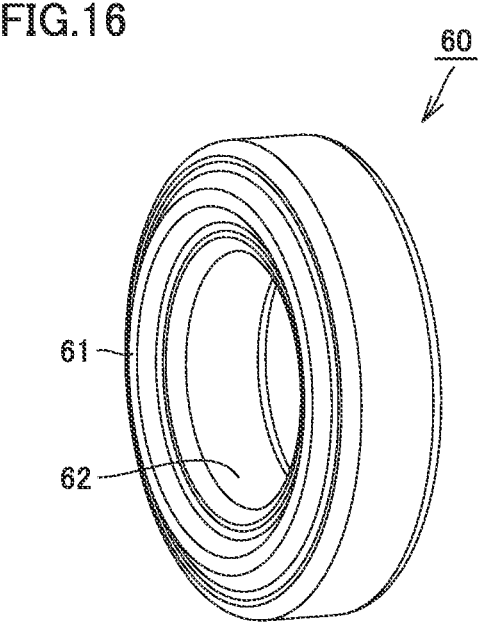
FIG. 16 is a perspective view of a packing of the syringe type ejection device according to the second embodiment.
Figure 17:
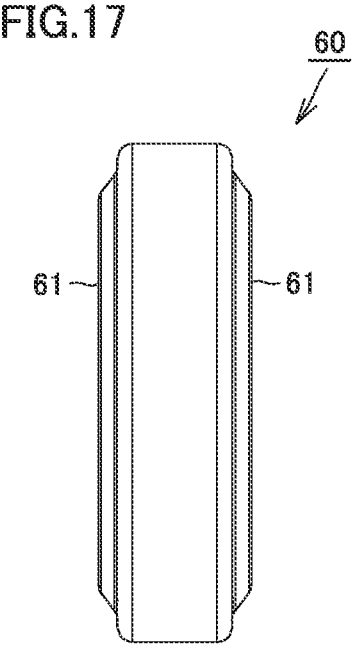
FIG. 17 is a side view of the packing of the syringe type ejection device according to the second embodiment.

FIG. 16 is a perspective view of a packing of the syringe type ejection device according to the second embodiment. FIG. 17 is a side view of the packing of the syringe type ejection device according to the second embodiment. As shown in FIGS. 16 and 17, packing 60 according to the second embodiment is formed to be thicker than packing 60 according to the first embodiment.

Increasing the thickness of packing 60 increases an amount of elastic deformation of packing 60 when packing 60 is pressed in the axial direction. As a result, packing 60 readily makes intimate contact with first surface 11f and second surface 35f.

Third Embodiment (Structure)

Figure 18:
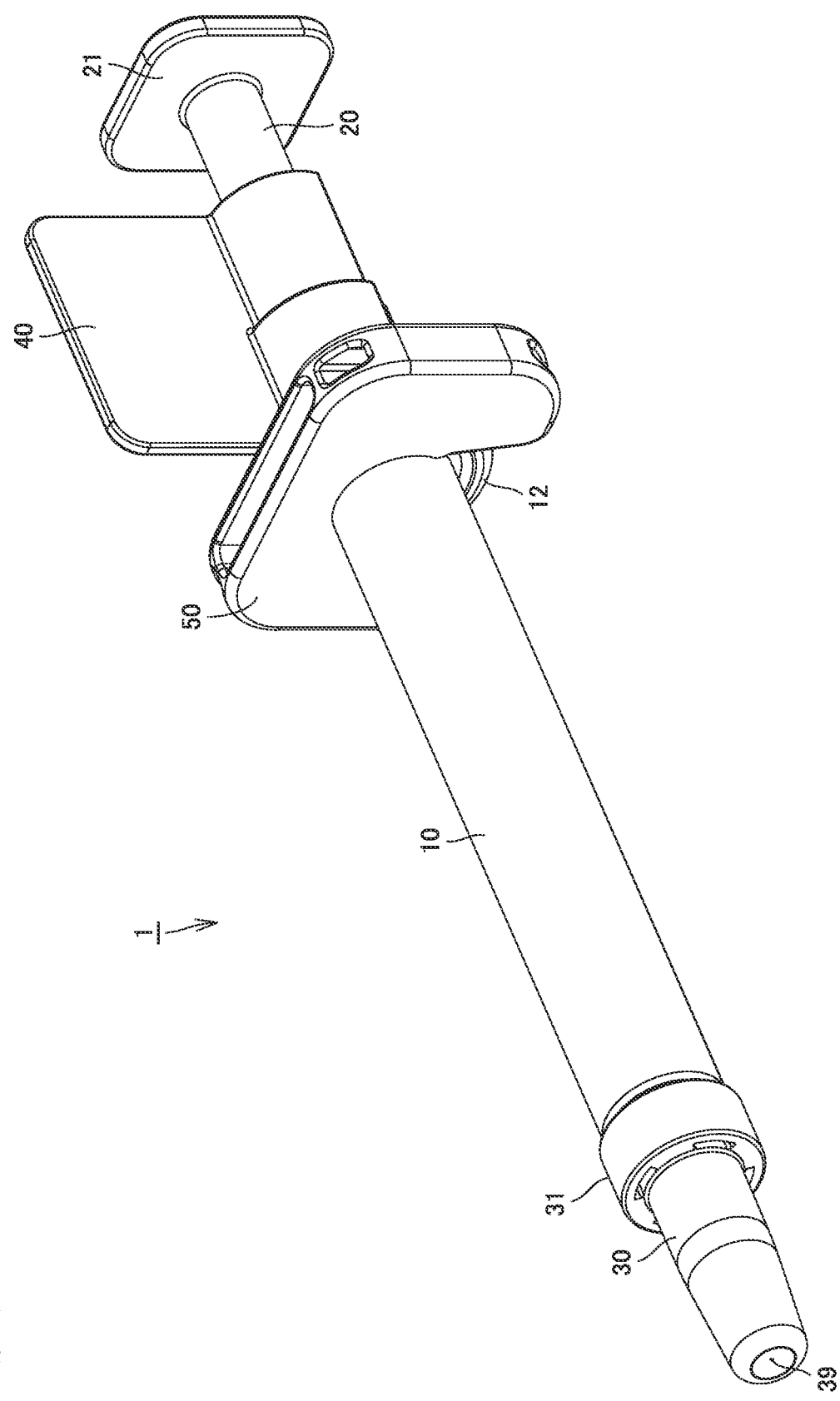
FIG. 18 is a perspective view of a syringe type ejection device according to a third embodiment.
Figure 19:
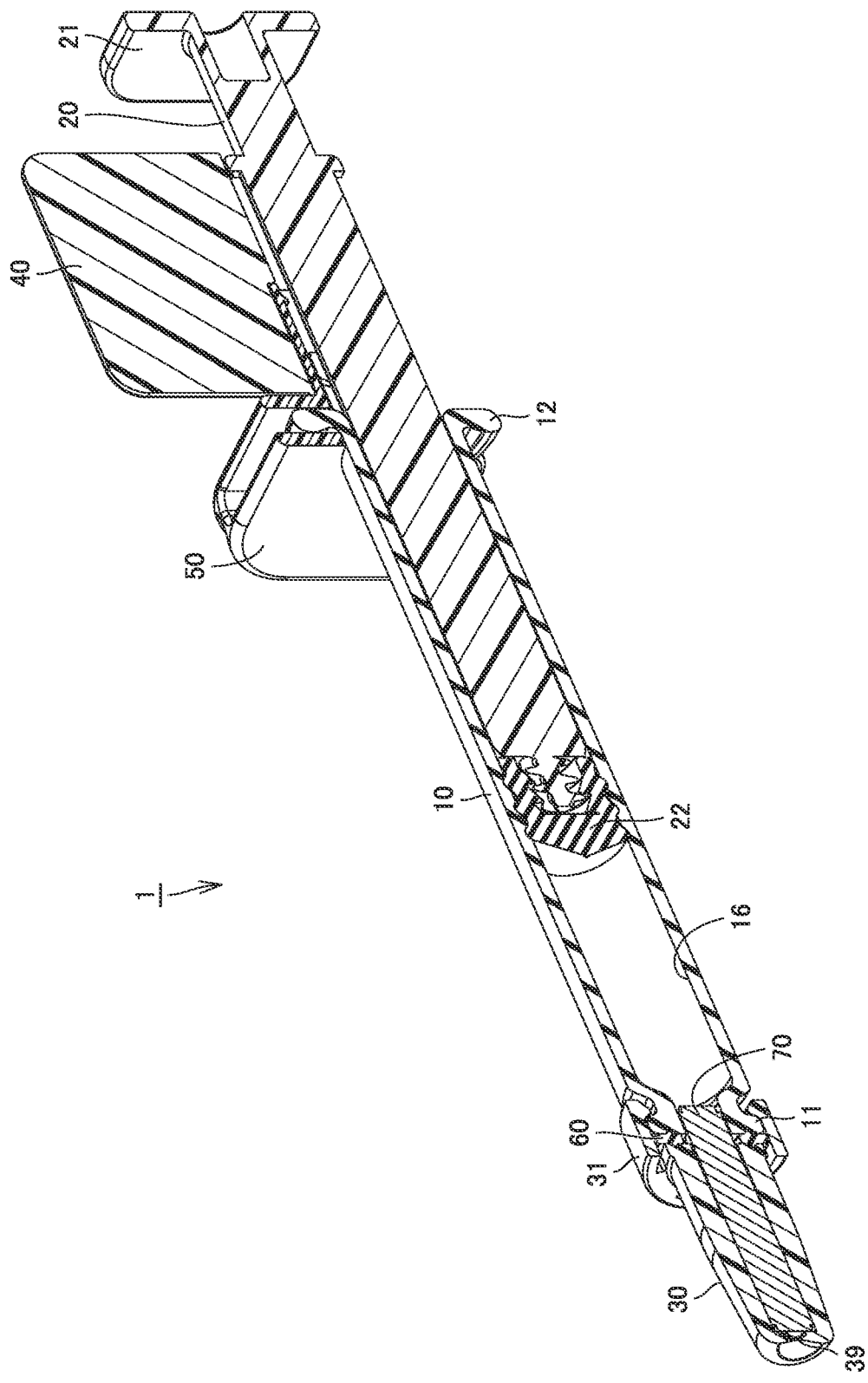
FIG. 19 is a perspective view including a partial cross section of the syringe type ejection device according to the third embodiment.

FIG. 18 is a perspective view of a syringe type ejection device according to a third embodiment. FIG. 19 is a perspective view including a partial cross section of the syringe type ejection device according to the third embodiment. As shown in FIGS. 18 and 19, syringe type ejection device 1 includes barrel 10, packing 60 as a seal member, nozzle 30, core 70, gasket 22, stopper 40, finger grip 50, and plunger 20.

Barrel 10 extends from large-diameter portion 11 as the tip end portion to flange 12. Barrel 10 is transparent or translucent. Barrel 10 is filled with liquid. Calibration marks indicating the amount of liquid may be provided on the outer circumferential surface of barrel 10.

Barrel 10 is made of glass, but may be made of plastic. The material for barrel 10 is determined depending on the liquid and the medicament stored in barrel 10.

Nozzle 30 is provided to face large-diameter portion 11. Nozzle 30 has biasing portion 31. Biasing portion 31 covers large-diameter portion 11. Nozzle 30 is provided with ejection hole 39 at its tip end. Core 70 is provided in its surface with a groove extending in a longitudinal direction of core 70. Thus, the liquid can move in the longitudinal direction of core 70 along the groove in the surface of core 70 even when core 70 is in contact with the inner circumferential surface of nozzle 30. The medicament in bore 16 can be ejected from ejection hole 39 through the groove in core 70.

Packing 60 is disposed between nozzle 30 and large-diameter portion 11. Packing 60 has an annular shape. Packing 60 is made of an elastic body such as rubber or resin.

Finger grip 50 fits over flange 12. Finger grip 50 is intended to be held by a human hand. Finger grip 50 does not need to be provided when flange 12 is large enough to be held by a human.

Plunger 20 is inserted in bore 16 in barrel 10. Plunger 20 is in the form of a bar. Gasket 22 fits over the tip end of plunger 20. The rear end of plunger 20 forms press portion 21.

Plunger 20 can move within barrel 10. The movement of plunger 20 within barrel 10 causes a change in volume of bore 16 from gasket 22 to large-diameter portion 11. The liquid is discharged from large-diameter portion 11 depending on this volume change.

Syringe type ejection device 1 is a capacity-defined syringe. Stopper 40 engages plunger 20. Stopper 40 serves to determine a dose of medicament by a single pumping. Stopper 40 is provided when the dose by a single pumping of plunger 20 needs to be limited. Stopper 40 does not need to be provided when the dose does not need to be limited.

When using syringe type ejection device 1 as a transnasal administration device, nozzle 30 is inserted in one of the nostrils and plunger 20 is pumped to eject the medicament from ejection hole 39. A stroke of the pumping is limited by stopper 40. Stopper 40 is removed from plunger 20, nozzle 30 is inserted in the other nostril and plunger 20 is pumped, to thereby eject the medicament into the other nostril from ejection hole 39.

Figure 20:
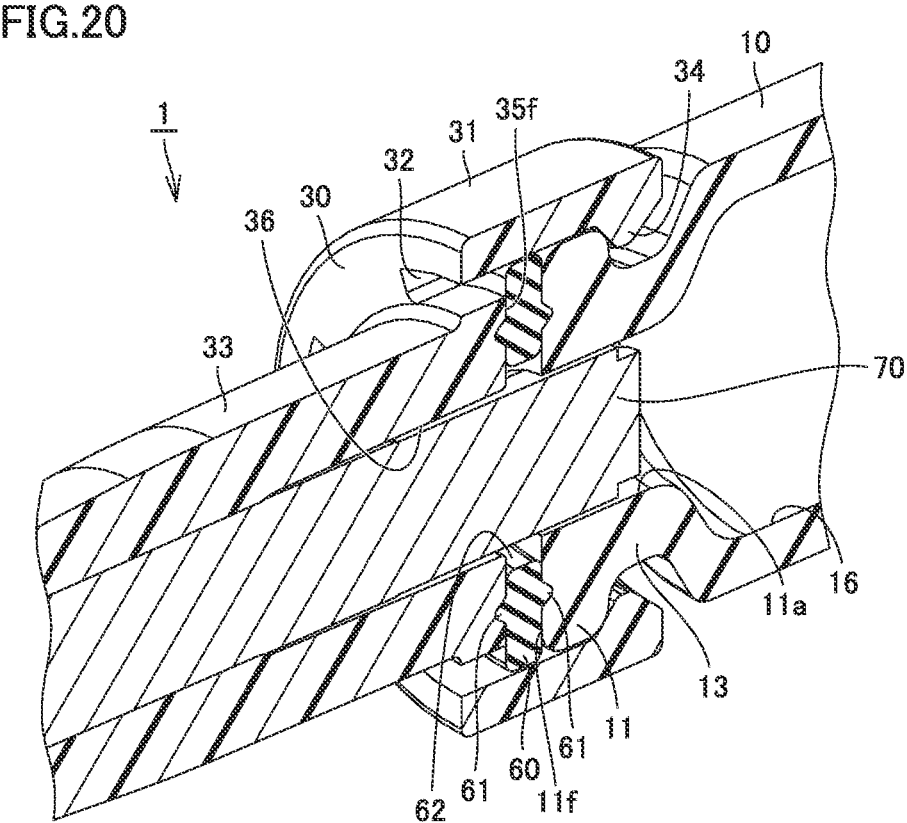
FIG. 20 is a perspective view including a partial cross section showing an enlarged engagement portion of a barrel and a nozzle of the syringe type ejection device according to the third embodiment.

FIG. 20 is a perspective view including a partial cross section showing an enlarged engagement portion of the barrel and the nozzle of the syringe type ejection device according to the third embodiment. As shown in FIG. 20, barrel 10 has neck 13 having a small outer diameter. Large-diameter portion 11 is attached to neck 13. Neck 13 and large-diameter portion 11 are provided with discharge space 11a.

First surface 11f of large-diameter portion 11 is a surface that makes contact with packing 60 as an O ring.

Nozzle body 33 of nozzle 30 is provided with holding space 36 which is a bore. Core 70 is stored in holding space 36. Core 70 is provided with a groove in its surface for delivering the medicament to the nozzle tip end. Core 70 protrudes from the rear end of nozzle 30. Thus, core 70 is inserted in large-diameter portion 11 and neck 13 at the tip end of barrel 10.

The rear end face of nozzle 30 is second surface 35f. Second surface 35f faces first surface 11f.

Biasing portion 31 forms part of nozzle 30. Biasing portion 31 is provided with hooks 34 that engage large-diameter portion 11. Nozzle 30 is provided with through holes 32. Biasing portion 31 is thereby provided with flexibility.

Figure 21:
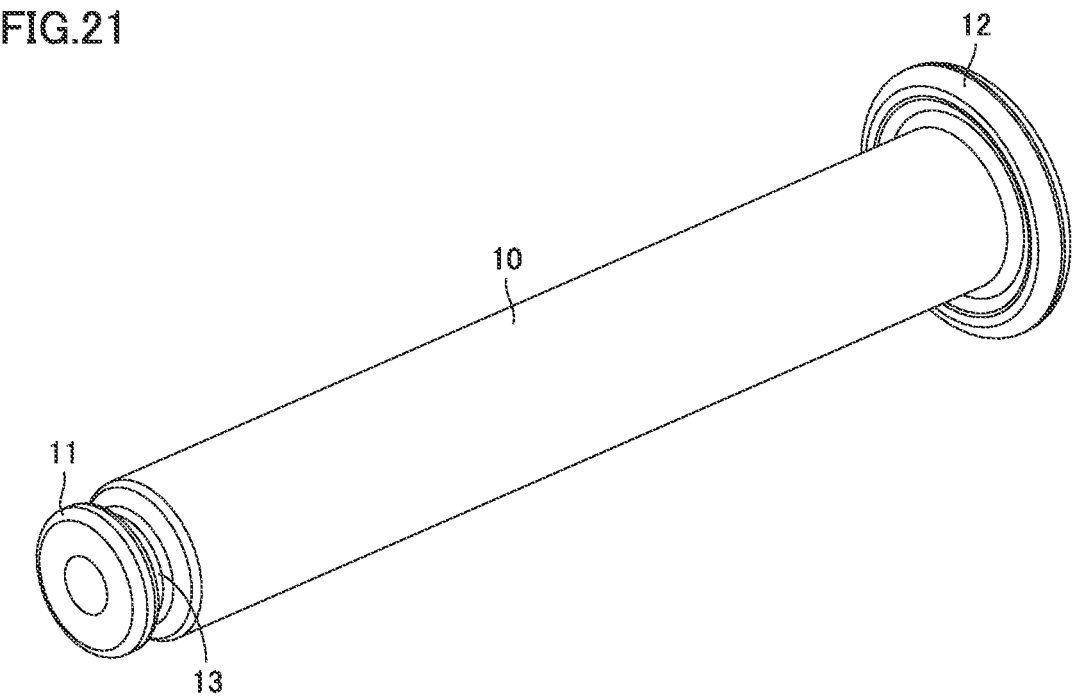
FIG. 21 is a perspective view of the barrel of the syringe type ejection device according to the third embodiment.

FIG. 21 is a perspective view of the barrel of the syringe type ejection device according to the third embodiment. Barrel 10 made of glass extends from large-diameter portion 11 to flange 12 in the longitudinal direction. Barrel 10 in a cylindrical shape has a constant inner diameter. Barrel 10 is not limited to have a cylindrical shape. The material for the barrel may be other than glass.

Figure 22:
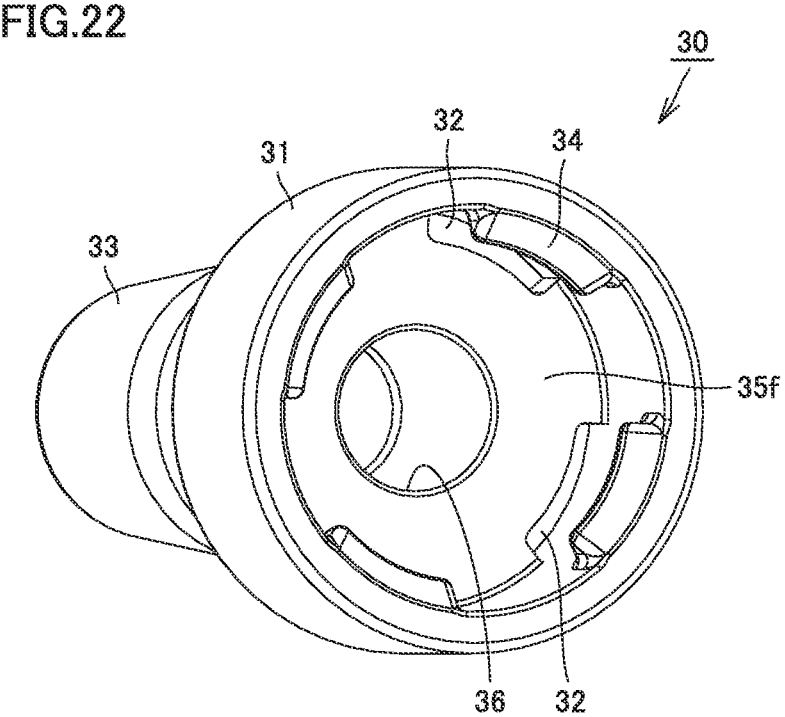
FIG. 22 is a perspective view of the nozzle of the syringe type ejection device according to the third embodiment.

FIG. 22 is a perspective view of the nozzle of the syringe type ejection device according to the third embodiment. As shown in FIG. 22, biasing portion 31 is at the rear end side of nozzle 30. Biasing portion 31 has an outer diameter greater than an outer diameter of nozzle body 33. The plurality of hooks 34 are provided at regular intervals in the inner space of biasing portion 31. Although biasing portion 31 is provided integrally with nozzle 30 in this embodiment, biasing portion 31 may be provided separately from nozzle 30.

The plurality of through holes 32 are provided in the outer circumference of second surface 35f. Each through hole 32 is provided at a position corresponding to each hook 34.

Figure 23:
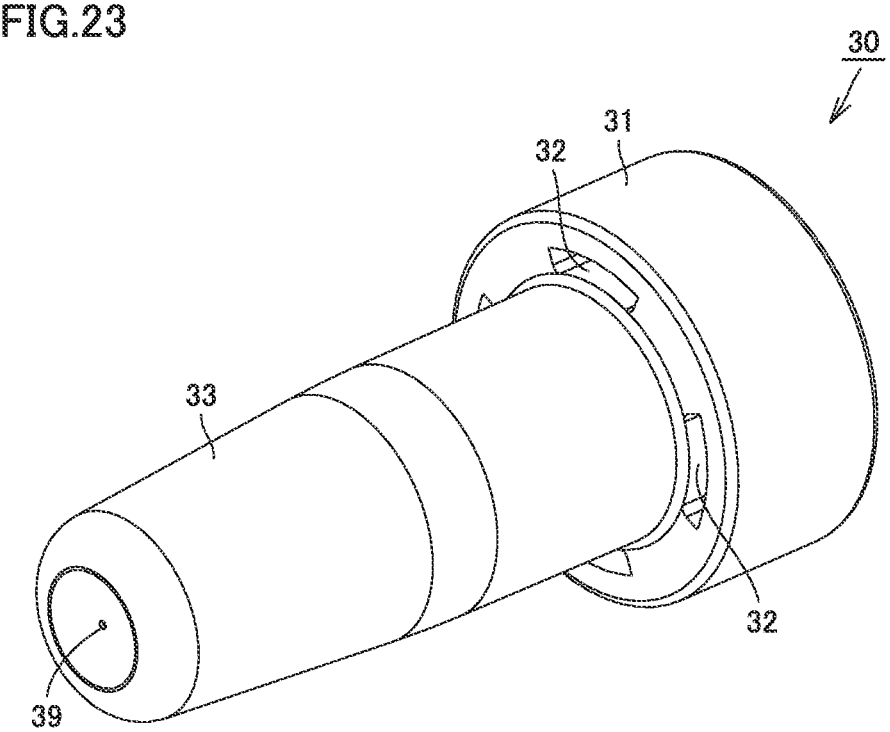
FIG. 23 is a perspective view of the nozzle of the syringe type ejection device according to the third embodiment.

FIG. 23 is a perspective view of the nozzle of the syringe type ejection device according to the third embodiment. As shown in FIG. 23, nozzle body 33 has an outer diameter that decreases toward its tip end, forming a so-called tapered shape. This is to allow the insertion of the tip end of nozzle body 33 in a nostril for ejection of the medicament into a nasal cavity.

FIG. 24 shows a perspective view (a) of the packing of the syringe type ejection device according to the third embodiment. FIG. 24 shows a side view (b) of the packing of the syringe type ejection device according to the third embodiment. As shown in (a) and (b) of FIG. 24, packing 60 has a circular shape, with through hole 62 provided at its center. Thrust surfaces of packing 60 facing each other are provided with the pair of annular convex portions 61. Because of the provision of convex portions 61, convex portions 61 are compressed by first surface 11f and second surface 35f to have a crushed shape. The effect of preventing leakage of the liquid is thereby increased.

Syringe type ejection device 1 includes barrel 10, nozzle 30 disposed to face barrel 10, and core 70 inserted in nozzle 30. Barrel 10 has large-diameter portion 11 as a tip end portion provided with discharge space 11a for discharging the liquid. Nozzle 30 is provided with holding space 36 for holding core 70, and holding space 36 is in communication with discharge space 11a. Core 70 is inserted in discharge space 11a. Syringe type ejection device 1 further includes annular packing 60 interposed between barrel 10 and nozzle 30. Large-diameter portion 11 includes first surface 11f facing nozzle 30. Nozzle 30 includes second surface 35f facing first surface 11f, annular packing 60 is provided to be in contact with first surface 11f and second surface 35f to enable movement of the liquid from discharge space 11a to holding space 36, and syringe type ejection device 1 further includes biasing portion 31 that biases first surface 11f and second surface 35f toward annular packing 60.

Biasing portion 31 is provided on nozzle 30. Biasing portion 31 covers large-diameter portion 11. Biasing portion 31 engages large-diameter portion 11. Biasing portion 31 has the plurality of hooks 34 that engage large-diameter portion 11. Biasing portion 31 is flexible, and through holes 32 extending through the thickness of nozzle 30 are provided in portions of the nozzle in proximity of biasing portion 31. First surface 11f and second surface 35f are thrust surfaces. Core 70 protrudes from second surface 35f and is inserted in discharge space 11a.

When plunger 20 is pushed toward nozzle 30, the medicament in bore 16 is moved through the groove provided in the surface of core 70 and ejected from ejection hole 39. When using syringe type ejection device 1 as a transnasal administration device, nozzle 30 is inserted in a nostril and the medicament is sprayed into a nasal cavity.

Figure 25:
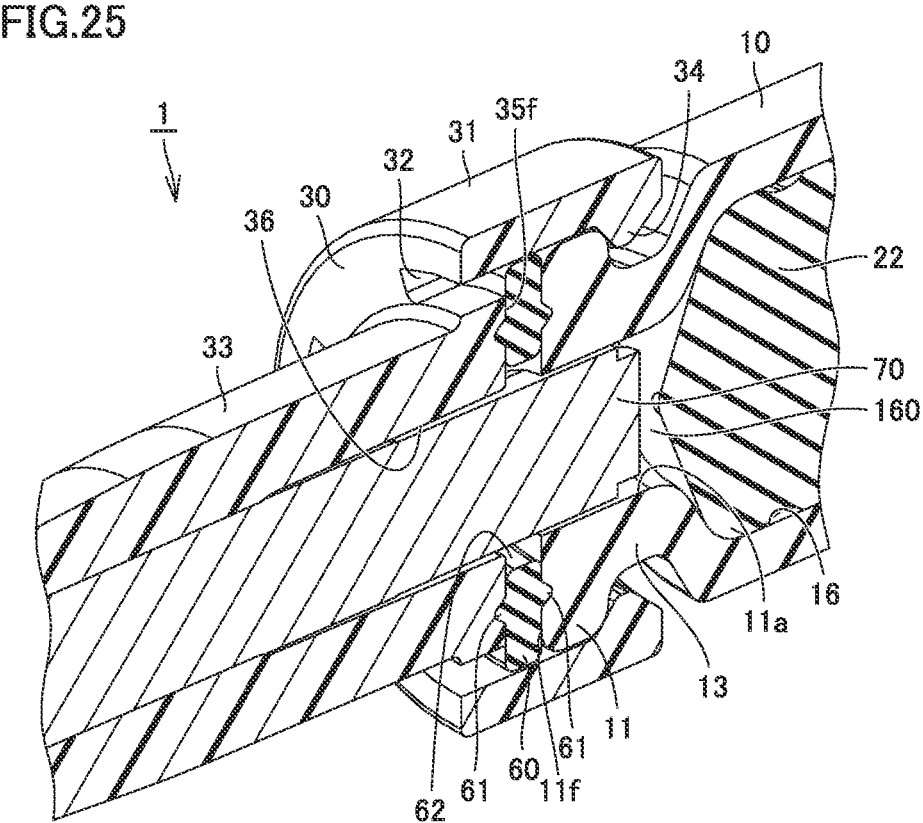
FIG. 25 is a perspective view including a partial cross section of the syringe type ejection device according to the third embodiment, illustrated to describe a residual liquid space.

FIG. 25 is a perspective view including a partial cross section of the syringe type ejection device according to the third embodiment, illustrated to describe a residual liquid space. As shown in FIG. 25, gasket 22 is at a position closer to core 70 after the spray. A residual liquid space 160 is formed between gasket 22 and core 70. The medicament (liquid) that was not sprayed remains in residual liquid space 160. With core 70 being inserted in discharge space 11a, residual liquid space 160 has a smaller volume than when core 70 is not inserted in discharge space 11a. When core 70 is not inserted in discharge space 11a, the medicament remains throughout discharge space 11a. In contrast, since core 70 is inserted in discharge space 11a, the amount of residual liquid in discharge space 11a can be reduced.

(Effects)

In syringe type ejection device 1 thus structured, with core 70 being inserted in discharge space 11a, the amount of residual liquid in discharge space 11a can be reduced.

Packing 60 is provided between first surface 11f and second surface 35f, and first surface 11f and second surface 35f are biased toward packing 60 by biasing portion 31. As a result, leakage of the liquid from between first surface 11f and second surface 35f can be prevented. As a result, a prescribed amount of medicament can be reliably sprayed.

Since first surface 11f and second surface 35f are thrust surfaces and packing 60 is disposed between them, the size in the radial direction of syringe type ejection device 1 can be made smaller than when packing 60 is provided on a radial surface. The inner diameter of discharge space 11a can be increased, thus making it easier to insert core 70 in the discharge space.

Since biasing portion 31 covers large-diameter portion 11, the area of contact between biasing portion 31 and large-diameter portion 11 is increased. As a result, large-diameter portion 11 can be reliably held by biasing portion 31.

Since the plurality of hooks 34 are flexible (elastic), and engage large-diameter portion 11 in the state shown in FIG. 20, the elasticity of biasing portion 31 can be utilized to press first surface 11f against packing 60.

Fourth Embodiment

Figure 26:
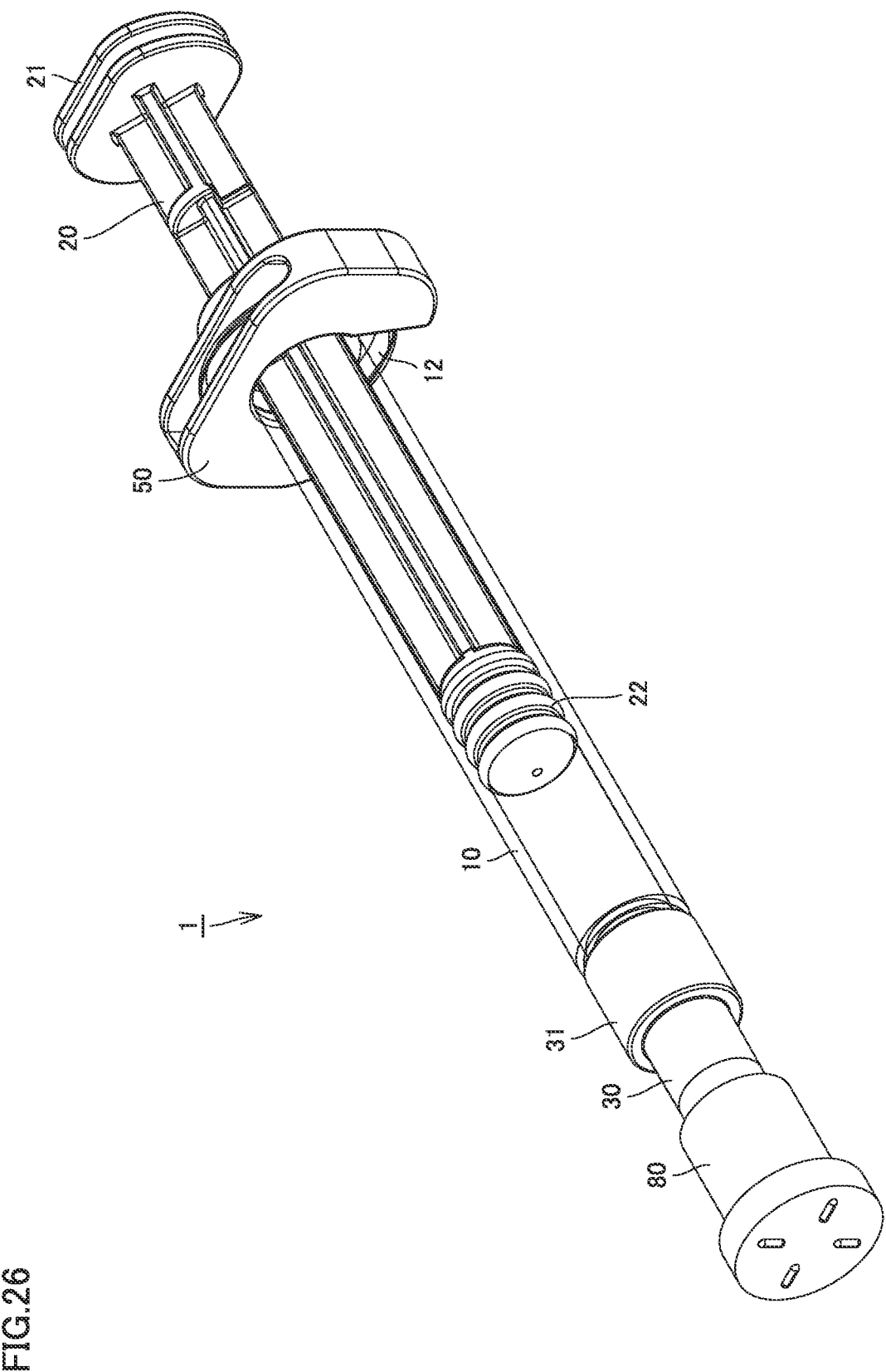
FIG. 26 is a perspective view of a syringe type ejection device according to a fourth embodiment.
Figure 27:
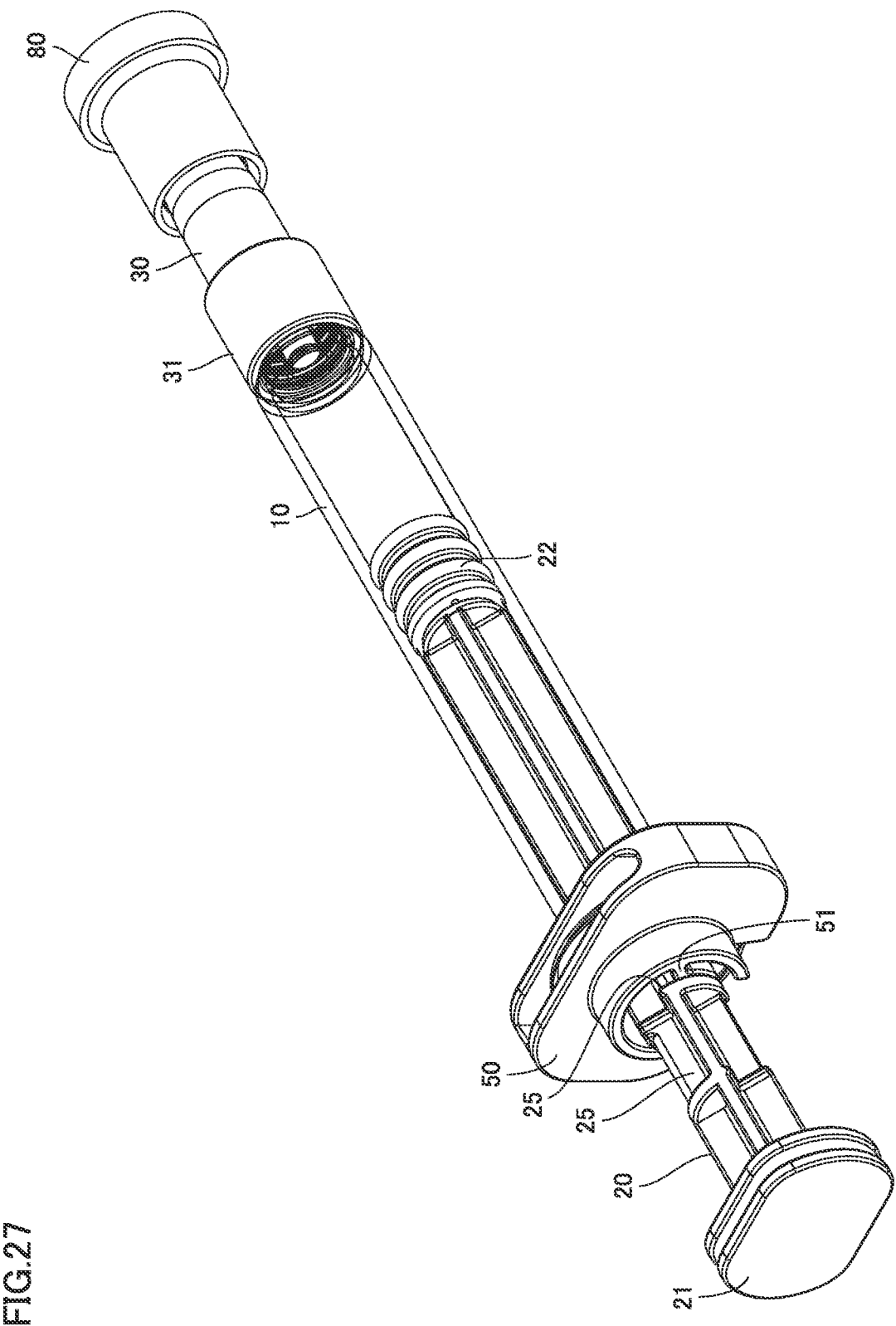
FIG. 27 is a perspective view of the syringe type ejection device according to the fourth embodiment.
Figure 28:
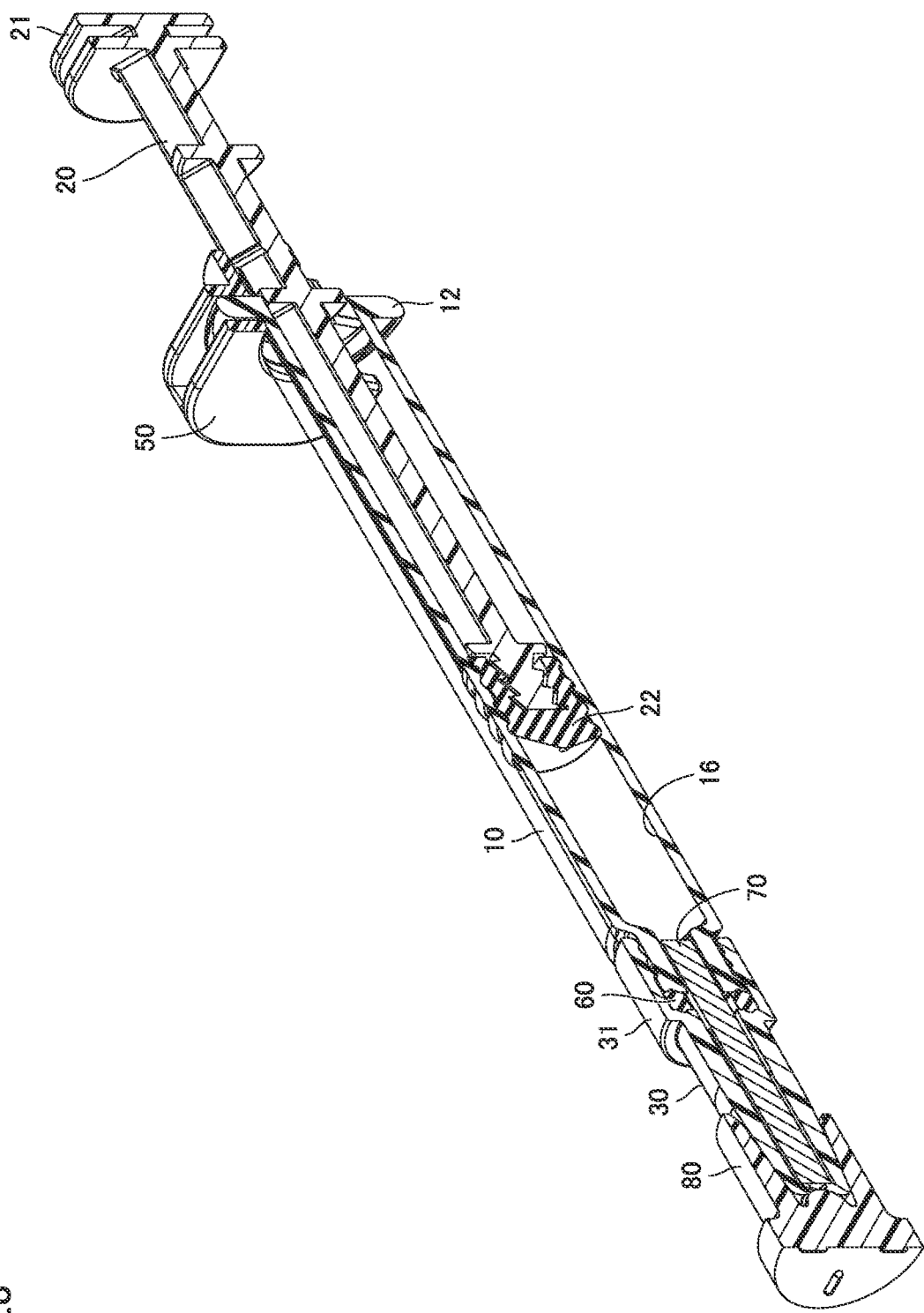
FIG. 28 is a perspective view including a partial cross section of the syringe type ejection device according to the fourth embodiment.

FIGS. 26 and 27 are perspective views of a syringe type ejection device according to a fourth embodiment. FIG. 28 is a perspective view including a partial cross section of the syringe type ejection device according to the fourth embodiment.

As shown in FIGS. 26 to 28, in syringe type ejection device 1 according to the fourth embodiment, plunger 20 is provided with step 25. Step 25 engages protrusion 51 of finger grip 50.

The engagement is released by rotation of plunger 20 from the state in which protrusion 51 and step 25 are in contact with each other as shown in FIG. 27. Plunger 20 can thereby be moved in the axial direction.

Nozzle cap 80 fits over the tip end of nozzle 30 in the fourth embodiment. Nozzle 30 may be covered with nozzle cap 80 in the third embodiment as well.

Figure 29:
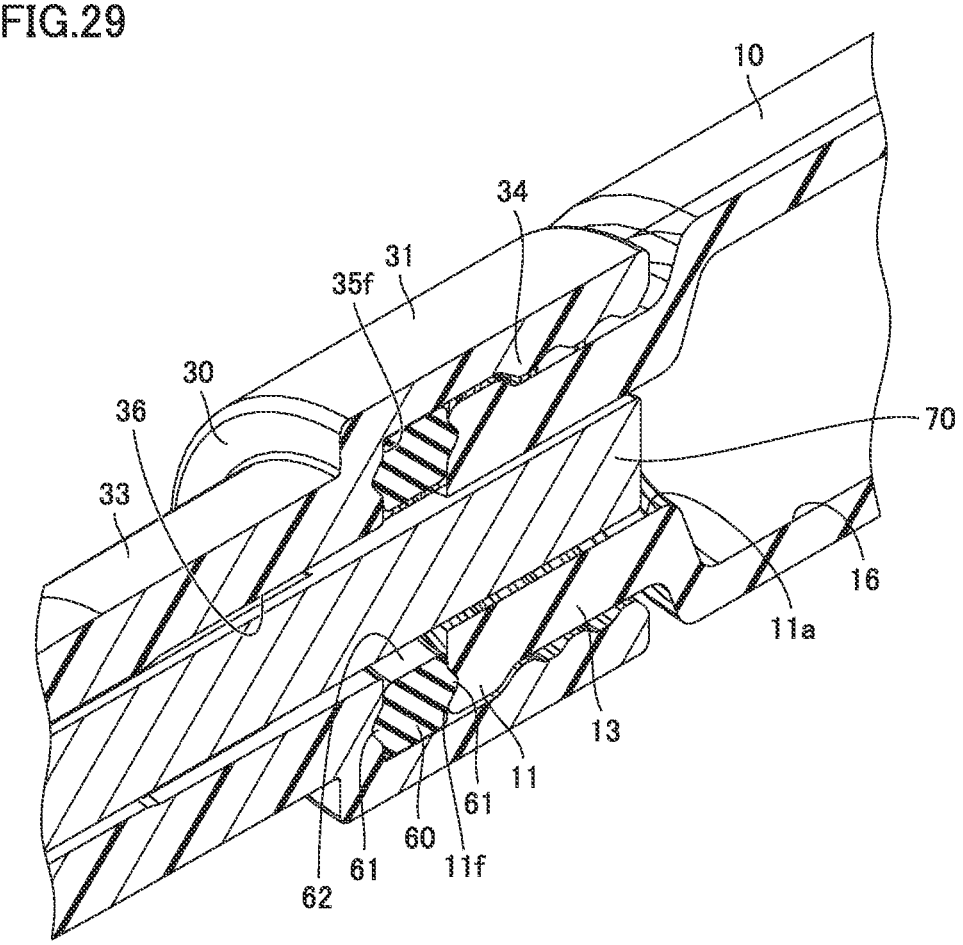
FIG. 29 is a perspective view including a partial cross section showing an enlarged engagement portion of a barrel and a nozzle of the syringe type ejection device according to the fourth embodiment.

FIG. 29 is a perspective view including a partial cross section showing an enlarged engagement portion of a barrel and the nozzle of the syringe type ejection device according to the fourth embodiment. As shown in FIG. 29, biasing portion 31 according to the fourth embodiment is longer than biasing portion 31 according to the third embodiment in the axial direction. Biasing portion 31 is provided with hooks 34 on its inner circumferential surface. Nozzle 30 is not provided with the through holes as were described in the third embodiment.

Figure 30:
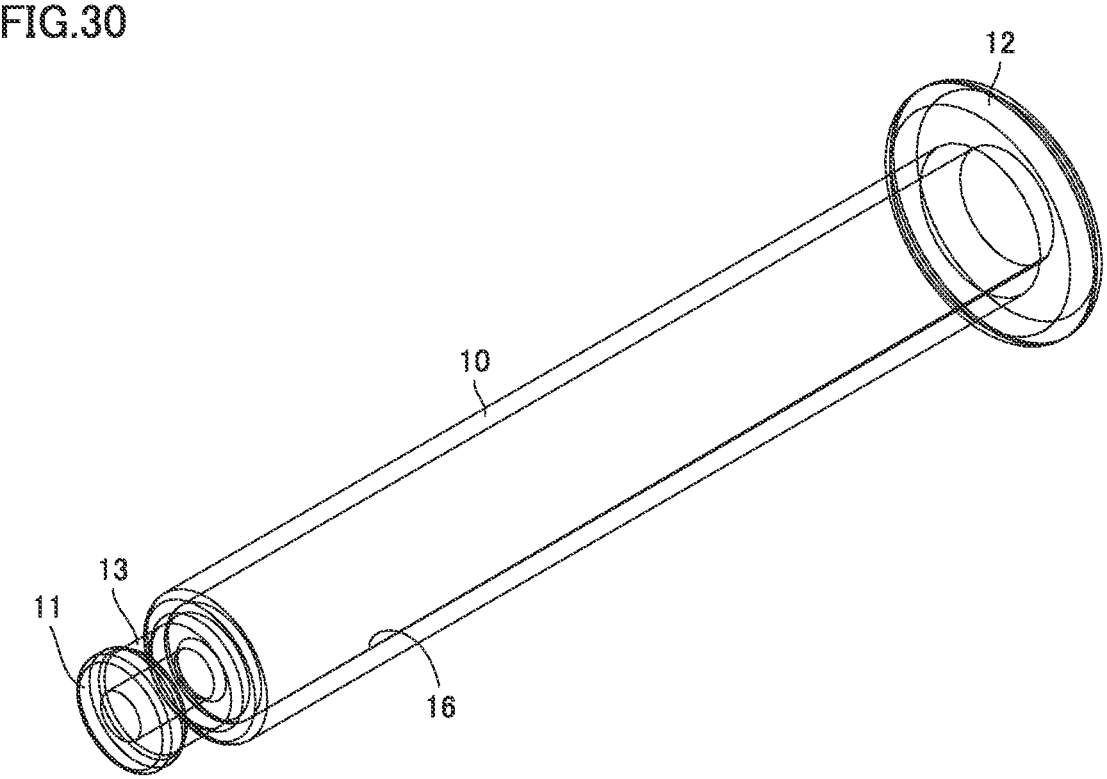
FIG. 30 is a perspective view of the barrel of the syringe type ejection device according to the fourth embodiment.

FIG. 30 is a perspective view of the barrel of the syringe type ejection device according to the fourth embodiment. As shown in FIG. 30, an internal structure of barrel 10 according to the fourth embodiment is shown in a perspective view.

When using liquid or a medicament that has to be kept away from light, barrel 10 is made of a light-shielding material.

Figure 31:
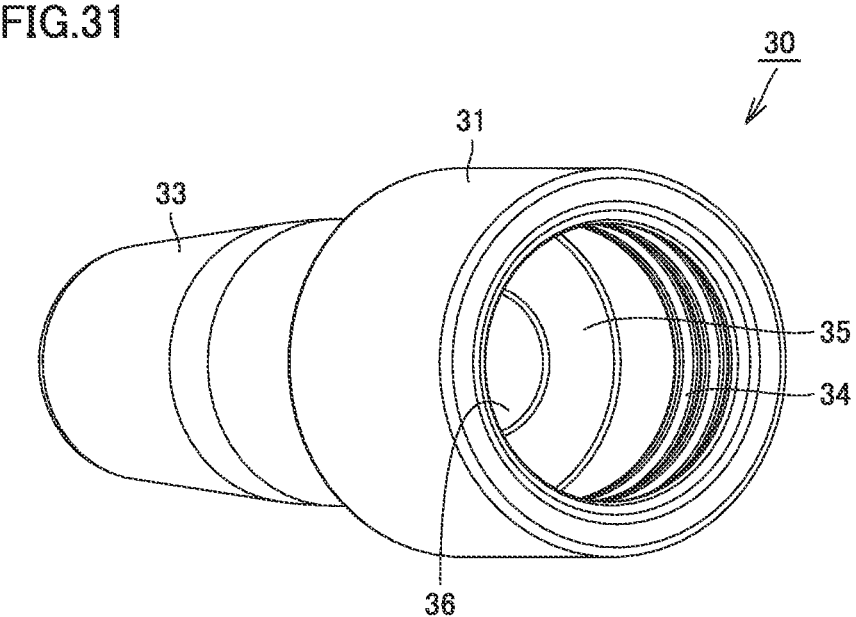
FIG. 31 is a perspective view of the nozzle of the syringe type ejection device according to the fourth embodiment.
Figure 32:
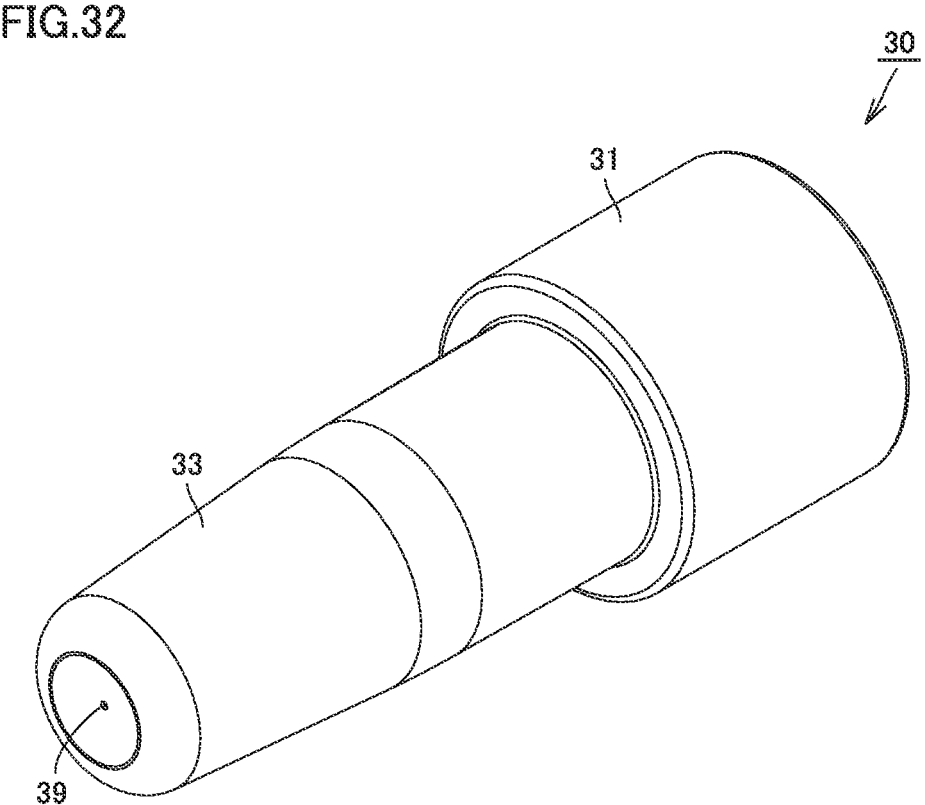
FIG. 32 is a perspective view of the nozzle of the syringe type ejection device according to the fourth embodiment.

FIGS. 31 and 32 are perspective views of the nozzle of the syringe type ejection device according to the fourth embodiment. As shown in FIGS. 31 and 32, nozzle 30 in the fourth embodiment has biasing portion 31 elongated in the axial direction. The difference from biasing portion 31 according to the third embodiment is that this biasing portion 31 is provided with annular hooks 34 on its inner circumferential surface.

FIG. 33 shows a perspective view (a) of a packing of the syringe type ejection device according to the fourth embodiment. FIG. 33 shows a side view (b) of the packing of the syringe type ejection device according to the fourth embodiment. As shown in (a) and (b) of FIG. 33, packing 60 according to the fourth embodiment is formed to be thicker than packing 60 according to the third embodiment.

Increasing the thickness of packing 60 increases an amount of elastic deformation of packing 60 when packing 60 is pressed in the axial direction. As a result, packing 60 readily makes intimate contact with first surface 11f and second surface 35f.

Figure 34:
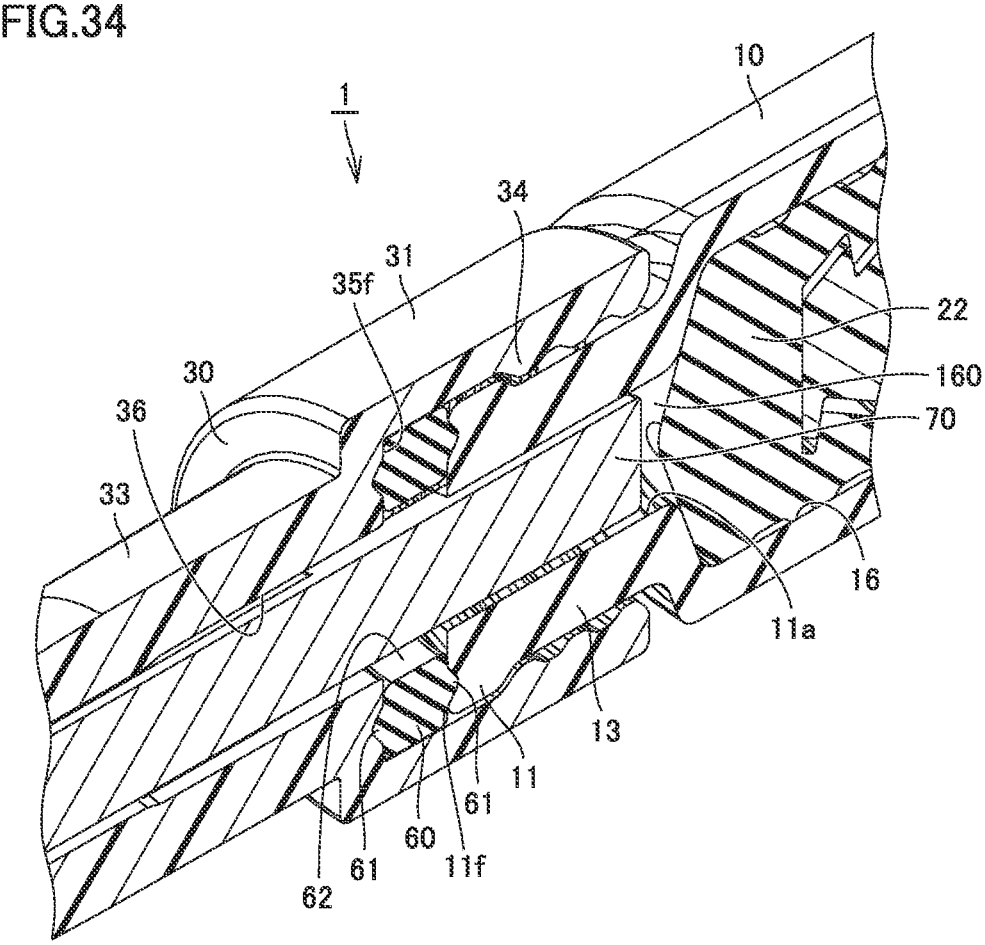
FIG. 34 is a perspective view including a partial cross section of the syringe type ejection device according to the fourth embodiment, illustrated to describe the residual liquid space.

FIG. 34 is a perspective view including a partial cross section of the syringe type ejection device according to the fourth embodiment, illustrated to describe the residual liquid space. As shown in FIG. 34, gasket 22 is at a position closer to core 70 after the spray. Residual liquid space 160 is formed between gasket 22 and core 70. The medicament (liquid) that was not sprayed remains in residual liquid space 160. With core 70 being inserted in discharge space 11a, residual liquid space 160 has a smaller volume than when core 70 is not inserted in discharge space 11a. When core 70 is not inserted in discharge space 11a, the medicament remains throughout discharge space 11a. In contrast, since core 70 is inserted in discharge space 11a, the amount of residual liquid in discharge space 11a can be reduced.

Fifth Embodiment

Figure 35:
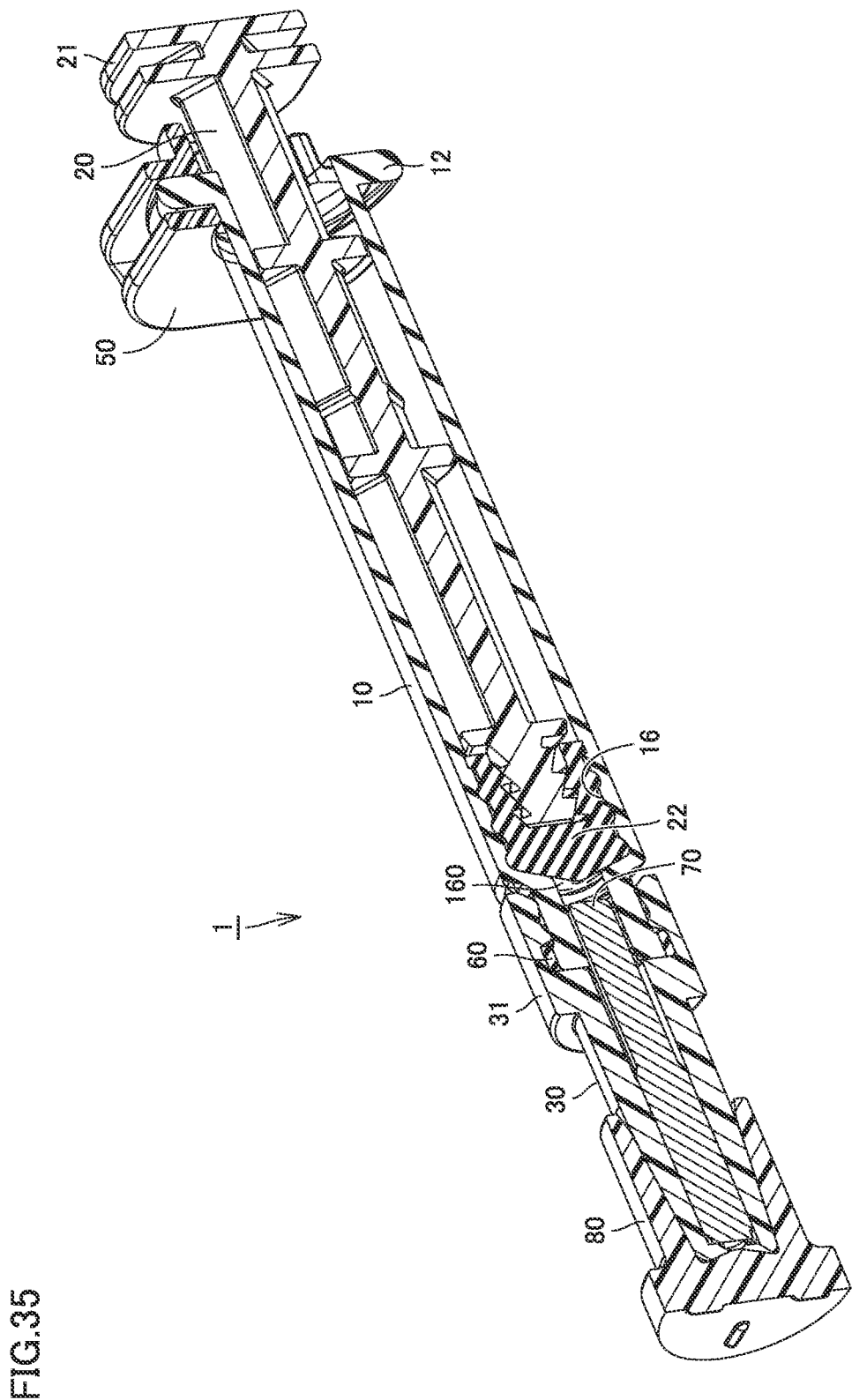
FIG. 35 is a perspective view including a partial cross section of a syringe type ejection device according to a fifth embodiment, illustrated to describe the residual liquid space.

FIG. 35 is a perspective view including a partial cross section of a syringe type ejection device according to a fifth embodiment, illustrated to describe the residual liquid space. As shown in FIG. 35, syringe type ejection device 1 in the fifth embodiment is different from syringe type ejection device 1 according to the fourth embodiment in that packing 60 is provided on an outer circumferential surface (radial surface) side of large-diameter portion 11.

Syringe type ejection device 1 thus structured according to the fifth embodiment also produces similar effects to those of syringe type ejection device 1 according to the fourth embodiment.

Sixth Embodiment

Figure 36:
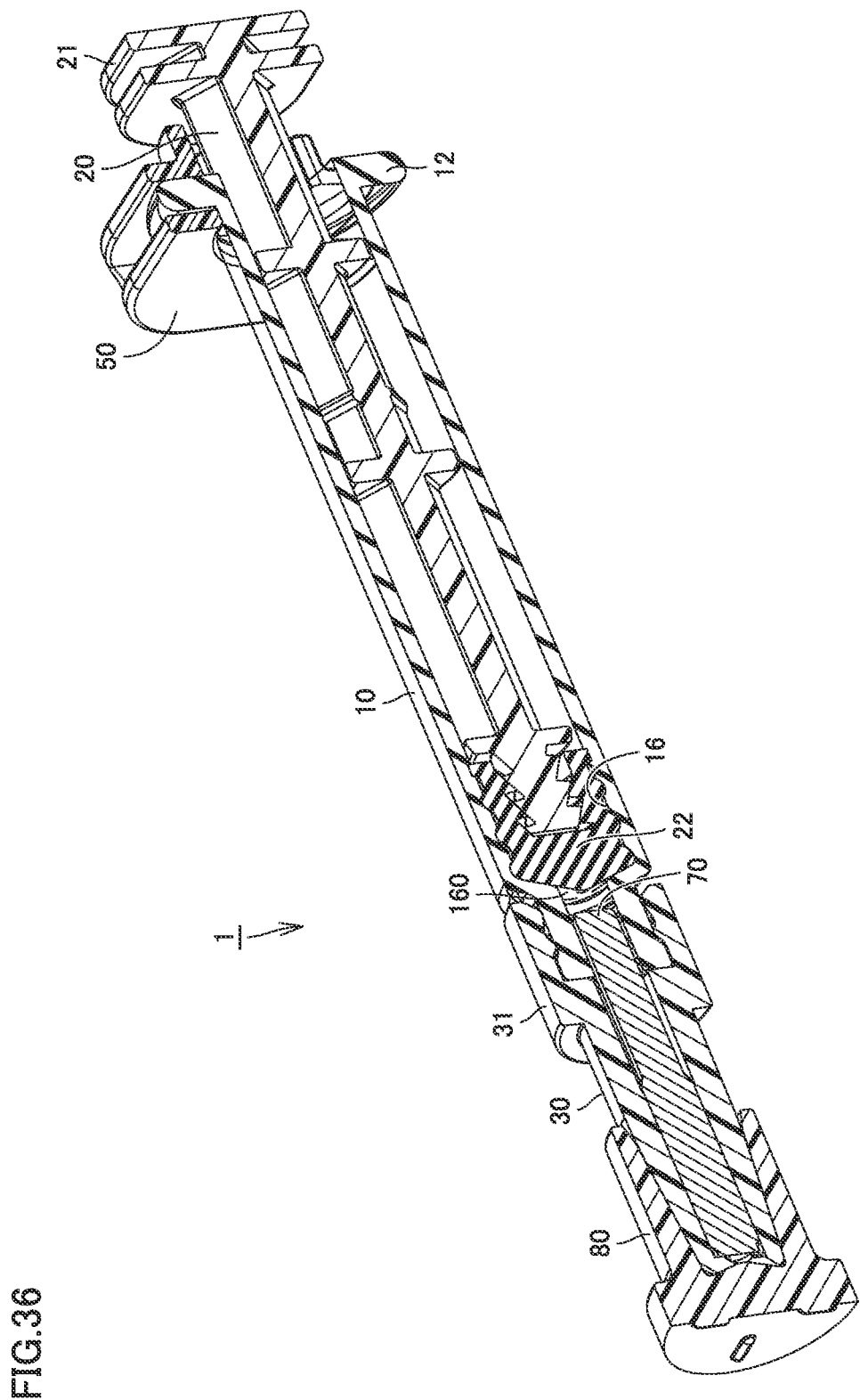
FIG. 36 is a perspective view including a partial cross section of a syringe type ejection device according to a sixth embodiment, illustrated to describe the residual liquid space.

FIG. 36 is a perspective view including a partial cross section of a syringe type ejection device according to a sixth embodiment, illustrated to describe the residual liquid space. As shown in FIG. 36, syringe type ejection device 1 in the sixth embodiment is different from syringe type ejection devices 1 according to the fourth and fifth embodiments in that packing 60 is not provided.

Syringe type ejection device 1 thus structured according to the sixth embodiment also produces similar effects to those of syringe type ejection device 1 according to the fourth embodiment.

Although the embodiments of the present invention have been described above, the embodiments disclosed herein are illustrative and non-restrictive in every respect. The scope of the present invention is defined by the terms of the claims, and is intended to include any modifications within the meaning and scope equivalent to the terms of the claims.

REFERENCE SIGNS LIST 1 syringe type ejection device; 10 barrel; 11 large-diameter portion; 11a discharge space; 11f first surface; 12 flange; 13 neck; 16 bore; 20 plunger; 21 press portion; 22 gasket; 25 step; 30 nozzle; 31 biasing portion; 32, 62 through hole; 33 nozzle body; 34 hook; 35f second surface; 36 holding space; 40 stopper; 50 finger grip; 51 protrusion; 60 packing; 61 convex portion; 70 core; 80 nozzle cap.

The invention claimed is:
1. A syringe type ejection device comprising:
a barrel;
a nozzle disposed to face the barrel; and
an annular packing interposed between the barrel and the nozzle,
the barrel having a tip end portion provided with a discharge space for discharging liquid, the tip end portion including a first surface facing the nozzle,
the nozzle being provided with a holding space for holding a core, the holding space being in communication with the discharge space, a rear end of the nozzle including a second surface, the second surface facing the first surface, the annular packing being provided to be in contact with the first surface and the second surface to enable movement of the liquid from the discharge space to the holding space, the syringe type ejection device further comprising a biasing portion that biases the first surface and the second surface toward the annular packing, the biasing portion is provided on the nozzle, the tip end portion has a large-diameter portion, the biasing portion is flexible and engages the large-diameter portion, and the biasing portion has a plurality of hooks that engage the large-diameter portion, a plurality of through holes extending through a thickness of the nozzle are provided in an outer circumference of the second surface and in a portion of the nozzle in proximity of the biasing portion.

2. The syringe type ejection device according to claim 1, wherein
the biasing portion covers the tip end portion.

3. The syringe type ejection device according to claim 1, wherein
the first surface and the second surface are thrust surfaces.

4. The syringe type ejection device according to claim 1, wherein
the core protrudes from the second surface and is inserted in the discharge space.

5. The syringe type ejection device according to claim 1, further comprising:
a core inserted in the nozzle,
the nozzle being provided with a holding space for holding the core, the holding space being in communication with the discharge space, and
the core being inserted in the discharge space.

6. The syringe type ejection device according to claim 1, wherein
the large-diameter portion of the tip end portion is a distal most end of the barrel, and the hooks are disposed at a proximal end of the biasing portion.

7. The syringe type ejection device according to claim 1, wherein
the large-diameter portion is uniformly biased by the hooks of the biasing portion to suppress leakage of the liquid.

8. The syringe type ejection device according to claim 1, wherein
the large-diameter portion is a flange shape.

* * * * *